US006342350B1

(12) United States Patent
Tanzi et al.

(10) Patent No.: US 6,342,350 B1
(45) Date of Patent: Jan. 29, 2002

(54) ALPHA-2-MACROGLOBULIN DIAGNOSTIC TEST

(75) Inventors: Rudolph E. Tanzi, Hull; Bradley T. Hyman, Swampscott; George W. Rebeck, Somerville; Deborah L. Blacker, Newton, all of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/148,503

(22) Filed: Sep. 4, 1998

Related U.S. Application Data

(60) Provisional application No. 60/093,297, filed on Jul. 17, 1998, and provisional application No. 60/057,655, filed on Sep. 5, 1997.

(51) Int. Cl.[7] .................................................. C12Q 1/68

(52) U.S. Cl. ........................................ 435/6; 435/91.2

(58) Field of Search .................. 435/6, 91.2; 536/24.33

(56) References Cited

U.S. PATENT DOCUMENTS

| | | | |
|---|---|---|---|
| 5,508,167 A | 4/1996 | Roses et al. .................... | 435/6 |
| 5,716,828 A | 2/1998 | Roses et al. .................... | 435/6 |
| 5,767,248 A | 6/1998 | Roses et al. ........... | 530/388.25 |
| 5,830,670 A | 11/1998 | De La Monte et al. ....... | 435/7.2 |
| 5,948,634 A | 10/1999 | De La Monte et al. .... | 435/69.1 |
| 5,948,888 A | 10/1999 | De La Monte et al. ..... | 530/350 |
| 6,071,705 A | 6/2000 | Wands et al. ................ | 435/7.1 |

FOREIGN PATENT DOCUMENTS

| | | |
|---|---|---|
| WO | WO 91/03557 | 3/1991 |
| WO | WO 92/03474 | 3/1992 |
| WO | WO 96/39834 | 12/1996 |
| WO | WO 99/11824 | 3/1999 |

OTHER PUBLICATIONS

Nielsen, K.L., et al., "Identification of residues in α–macroglobulins important for binding to the α–2–macroglobulin receptor/low density lipoprotein receptor–related protein," *J. Biol. Chem.* 271:12909–12912 (1996).
Soto, C., et al., "β–Sheet breaker peptides inhibit fibrillogenesis in a rat brain model of amyloidosis: Implications for Alzheimer's therapy," *Nature Med.* 4:822–826 (1988).
International Search Report for International Application No. PCT/US00/02412, mailed Jul. 6, 2000.
"Freely Associating," *Nature Genetics* 22:1–2 (May 1999).
Alvarez, V., et al., "Association between an α2 Macroglobulin DNA Polymorphism and Late–Onset Alzheimer's Disease," *Biochem. and Biophys. Res. Comm.* 264:48–50 (1999).
Blacker, D., et al., "Correspondence," *Nature Genetics* 22:21–22 (May 1999).
Chen, L., et al., "Apolipoprotein E promoter and α–2–Macroglobulin Polymorphisms are not Genetically Associated with Chinese late onset Alzheimer's Disease," *Neuroscience Letters* 269:173–177 (1999).
Dodel, R.C., et al., "α–2 Macroglobulin and the Risk of Alzheimer's Disease," *Neurology* 54:438–442 (2000).
Dow, D.J., et al., "α–2 Macroglobulin Polymorphism and Alzheimer Disease risk in the UK," *Nature Genetics* 22:16–17 (May 1999).
Du, Y., et al., "$\alpha_2$–Macroglobulin Attenuates β–Amyloid Peptide 1–40 Fibril Formation and Associated Neurotoxicity of Cultured Fetal Rat Cortical Neurons," *J. of Neurochem.* 70:1182–1188 (1998).
Gauderman, W.J., et al., "Family–Based Association Studies," *Monogr. Natl. Canc. Inst.* 26:31–37 (1999).
Hampe, J., et al., "Genes for Polygenic Disorders: Considerations for Study Design in the Complex Trait of Inflammatory Bowel Disease," *Hum. Hered.* 50:91–101 (Mar.–Apr. 2000).
Horvath, S., and Laird, N.M., "A Discordant–Sibship Test for Disequilibrium and Linkage: No Need for Parental Data," *Am. J. Hum. Genet.* 63:1886–1897 (Dec. 1998).
Kovács, T., et al., "Alpha–2–Macroglobulin Intronic Polymorphism is not associated with Autopsy–confirmed late–onset Alzheimer Disease," *Neurosci. Lett.* 273:61–63 (1999).
Korovaitseva, G.I., et al., "Alpha–2 Macroglobulin Gene in early– and late–onset Alzheimer Disease," *Neurosci. Lett.* 271:129–131 (1999).
Myllykangas, L., et al., "Genetic Association of $\alpha_2$–Macroglobulin with Alzheimer's Disease in a Finnish Elderly Population," *Ann. of Neuro.* 46(3):382–390 (1999).
Rogaeva, E.A., et al., "An α–2 macroglobulin Insertion–Deletion Polymorphism in Alzheimer's Disease," *Nature Genetics* 22:19–22 (May 1999).
Romas, S.N., et al., "The Deletion polymorphism and Val1000Ile in α–2–macroglobulin and alzheimer Disease in Carribbean Hispanics," *Neurosci. Lett.* 279:133–136 (2000).
Rudrasingham, V., et al., "α–2 Macroglobulin Gene and Alzheimer Disease," *Nature Genetics* 22:17–19 (May 1999).

(List continued on next page.)

*Primary Examiner*—Lisa B. Arthur
(74) *Attorney, Agent, or Firm*—Sterne, Kessler, Goldstein & Fox P.L.L.C.

(57) ABSTRACT

The disclosed invention relates to a diagnostic method for Alzheimer's disease based on genotyping the Alpha-2-Macroglobulin locus. A statistically significant correlation was found between inheritance of particular alleles of the Alpha-2-Macroglobulin gene and the occurrence of Alzheimer's disease. The diagnostic method involves the isolation of nucleic acid from an individual and subsequent genotyping by means such as sequencing or restriction fragment length polymorphism analysis. The invention also provides a means of genotype analysis through protein isotyping Alpha-2-Macroglobulin variant proteins. Finally, kits for nucleic acid analysis or protein analysis are taught.

10 Claims, 3 Drawing Sheets

OTHER PUBLICATIONS

Shibata, N., et al., "Genetic Association between alpha–2–macroglobulin and Japanese Sporadic Alzheimer's Disease," *Neurosci. Lett. 271*:132–134 (1999).

Singleton, A.B., et al., "α–Macroglobulin polymorphisms in Alzheimer's Disease and Dementia with Lewy Bodies," *NeuroReport 10(7)*:1507–1510 (May 1999).

Sodeyama, N. et al., "α2–Macroglobulin Polymorphism is not Associated with AD or AD–type Neuropathology in the Japanese," *Neurology 54(2)*:443–446 (2000).

Hu et al. (1999) Neurology 53(3) 642–3.*

Crawford et al. Neuroscience Letters (1999) 270(3): 133–6.*

Blacker, D., and Tanzi, R.E., "The Genetics of Alzheimer Disease. Current Status and Future Prospects," *Arch. Neurol. 55*:294–296 (Mar. 1998).

Justus, C.W.E., et al., "Quantification of free $\alpha_2$–macroglobulin and $\alpha_2$–macroglobulin–protease complexes by a novel ELISA system based on streptococcal $\alpha_2$–macroglobulin receptors," *J. Immunol. Meth. 126*:103–108 (Jan. 1990).

Poller, W., et al., "Sequence polymorphism in the human alpha–2–macroglobulin (A2M) gene," *Nucl. Acids Res. 19*:198 (Jan. 1991).

Schellenberg, G.D., "Genetic dissection of Alzheimer disease, a heterogeneous disorder," *Proc. Natl. Acad. Sci. USA 92*:8552–8559 (Sep. 1995).

International Search Report for International Application No. PCT/US98/18535, mailed Dec. 23, 1998.

Liao, A. et al., "Genetic association of an α2–macroglobulin (VAl1000Ile) polymorphism and Alzheimer's disease," *Hum. Mol. Gen. 7*:1953–1956 (Nov. 1998).

Stratagene, 1998 Catalog, "Gene Characterization Kits", La Jolla, CA (Feb. 1997).

Wavrant–DeVrièze, F. et al., "No association between the alpha–2 macroglobulin I1000V polymorphism and Alzheimer's disease," *Neur. Letts. 262*:137–139 (Mar. 1999).

Barrett, A.J., et al., "The Electrophoretically 'Slow' and 'Fast' Forms of the $\alpha_2$–Macroglobulin Molecule," *Biochem. J. 181*:401–418 (Aug. 1979).

Bauer, J., et al., "Interleukin–6 and α–2–macroglobulin indicate an acute–phase state in Alzheimer's disease cortices," *FEBS 285*:111–114 (Jul. 1991).

Blacker, D., et al., "ApoE–4 and age at onset of Alzheimer's disease: The NIHM Genetics Initiative," *Neurol. 48*:139–147 (Jan. 1997).

Blacker, D., et al., "Alpha–2 macroglobulin is genetically associated with Alzheimer disease," *Nat. Genet. 19*:357–360 (Aug. 1998).

Borth, W., "$\alpha_2$–Macroglobulin, a multifunctional binding protein with targeting characteristics," *FASEB J. 6*:3345–3353 (Dec. 1992).

Bowen, M.E., and Gettins, P.G.W., "Bait Region Involvement in the Dimer–Dimer Interface of Human $\alpha_2$–Macroglobulin and in Mediating Gross Conformational Change: Evidence From Cysteine Variants That Form Interdimer Disulfides," *J. Biol. Chem. 273*:1825–1831 (Jan. 1998).

Bretaudiere, J.–P., et al., "Structure of native $\alpha_2$–macroglobulin and its transformation to the protease bound form," *Proc. Natl. Acad. Sci. USA 85*:1437–1441 (Mar. 1988).

Businaro, R., et al., "Synthesis and secretion of $\alpha_2$–macroglobulin by human glioma established cell lines," *Exp. Brain Res. 88*:213–218 (Jan. 1992).

Clatworthy, A.E., et al., "Lack of Association of a Polymorphism in the Low–density Lipoprotein Receptor–Related Protein Gene With Alzheimer Disease," *Arch. Neurol. 54*:1289–1292 (Oct. 1997).

Devriendt, K., et al., "A cluster of $\alpha_2$–macroglobulin–related genes ($\alpha_2$M) on human chromosome 12p: cloning of the pregnancy–zone protein gene and an $\alpha_2$M pseudogene," *Gene 81*:325–334 (Sep. 1989).

Du, Y., et al., "$\alpha_2$–Macroglobulin as a β–Amyloid Peptide–Binding Plasma Protein," *J. Neurochem. 69*:299–305 (Jul. 1997).

Du, Y., et al., "$\alpha_2$–Macroglobulin Attenuates β–Amyloid Peptide 1–40 Fibril Formation and Associated Neurotoxicity of Cultured Fetal Rat Cortical Neurons," *J. Neurochem. 70*:1182–1188 (Mar. 1998).

Farrer, L.A., et al., "Transmission and age–at–onset patterns in familial Alzheimer's disease: Evidence for heterogeneity," *Neurol. 40*:395–403 (Mar. 1990).

Farrer, L.A., et al., "Effects of Age, Sex, and Ethnicity on the Association Between Apolipoprotein E Genotype and Alzheimer Disease: A Meta–analysis," *JAMA 278*:1349–1356 (Oct. 1997).

Feldman, S.R., et al., "Model of $\alpha_2$–macroglobulin structure and function," *Proc. Natl. Acad. Sci. USA 82*:5700–5704 (Sep. 1985).

Ganter, U., et al., "Alpha 2–macroglobulin synthesis in interleukin–6–stimulated human neuronal (SH–SY5Y neuroblastoma) cells," *FEBS 282*:127–131 (Apr. 1991).

Gómez–Isla, T., et al., "Neuronal Loss Correlates with but Exceeds Neurofibrillary Tangles in Alzheimer's Disease," *Ann. Neurol. 41*:17–24 (Jan.–Jun. 1997).

Hughes, S.R., et al., "$\alpha_2$–macroglobulin associates with β–amyloid peptide and prevents fibril formation," *Proc. Natl. Acad. Sci. USA 95*:3275–3280 (Mar. 1998).

Kan, C.–C., et al., "Nucleotide sequence of cDNA encoding human $\alpha_2$–macroglobulin and assignment of the chromosomal locus," *Proc. Natl. Acad. Sci. USA 82*:2282–2286 (Apr. 1985).

Kang, D.E., et al., "Genetic association of the low–density lipoprotein receptor–related protein gene (LPR), an apolipoprotein E receptor, with late–onset Alzheimer's disease," *Neurol. 49*:56–61 (Jul. 1997).

Krauter, K., et al., "A second–generation YAC contig map of human chromosome 12," *Nature 377 (Supp.)*:321–333 (Sep. 1995).

Kruglyak, L., et al., "Parametric and Nonparametric Linkage Analysis: A Unified Multipoint Approach," *Am. J. Hum. Genet. 58*:1347–1363 (Jun. 1996).

Lambert, J.–C., et al., "A new polymorphism in the APOE promoter associated with risk of developing Alzheimer's Disease," *Hum. Mol. Genet. 7*:533–540 (Mar. 1998).

Lendon, C.L., et al., "Genetic association studies between dementia of the Alzheimer's type and three receptors for apolipoprotein E in a Caucasian population," *Neurosci. Letters 222*:187–190 (Feb. 1997).

Lopes, M.B.S., et al., "Expression of $\alpha_2$–macroglobulin receptor/low denisty lipoprotein receptor–related protein is increased in reactive and neoplastic glial cells," *FEBS Letters 338*:301–305 (Feb. 1994).

Marynen, P., et al., "A genetic polymorphism in a functional domain of human pregnancy zone protein: the bait region. Genomic structure of the bait domains of human pregnancy zone protein and $\alpha_2$ macroglobulin," *FEBS 262*:349–352 (Mar. 1990).

Matthijs, G., and Marynen, P., "A deletion polymorphism in the human alpha–2–macroglobulin (A2M) gene," *Nucl. Acids. Res. 19:*5102 (Sep. 1991).

Mori, T., et al., "$\alpha_2$–Macroglobulin is an astroglia–derived neurite–promoting factor for cultured neurons from rat central nervous system," *Brain Res. 527:*55–61 (Sep. 1990).

Narita, M., et al., "$\alpha_2$–Macroglobulin Complexes with and Mediates the Endocytosis of β–Amyloid Peptide via Cell Surface Low–Density Lipoprotein Receptor–Related Protein," *J. Neurochem. 69:*1904–1911 (Nov. 1997).

Orita, M., et al., "Detection of polymorphisms of human DNA by gel electrophoresis as single–strand conformation polymorphisms," *Proc. Natl. Acad. Sci. USA 86:*2766–2770 (Apr. 1989).

Payami, H., et al., "A Prospective Study of Cognitive Health in the Elderly (Oregon Brain Aging Study): Effects of Family History and Apolipoprotein E Genotype," *Am. J. Hum. Genet. 60:*948–956 (Apr. 1997).

Pericak–Vance, M.A., et al., "Complete Genomic Screen in Late–Onset Familial Alzheimer Disease: Evidence for a New Locus on Chromosome 12," *JAMA 278:*1237–1241 (Oct. 1997).

Poller, W., et al., "Cloning of the human $\alpha_2$–macroglobulin gene and detection of mutations in two functional domains: the bait region and the thiolester site," *Hum. Genet. 88:*313–319 (Jan. 1992).

Qiu, W.Q., et al., "Degradation of Amyloid β–Protein by a Serine Protease–$\alpha_2$–Macroglobulin Complex," *J. Biol. Chem. 271:*8443–8451 (Apr. 1996).

Rebeck, G.W., et al., "Multiple, Diverse Senile Plaque–associated Proteins Are Ligands of an Apolipoprotein E Receptor, the $\alpha_2$–Macroglobulin Receptor/Low–Density–Lipoprotein Receptor–related Protein," *Ann. Neurol. 37:*211–217 (Feb. 1995).

Sottrup–Jensen, L., et al., "Primary Structure of Human $\alpha_2$–Macroglobulin: V. The Complete Structure," *J. Biol. Chem. 259:*8318–8327 (Jul. 1984).

Spielman, R.S., and Ewens, W.J., "Transmission/disequilibrium test (TDT) for linkage and linkage disequilibrium between disease and marker," Abstract No. 863, *Am. J. Hum. Genet. Suppl. 53* (Sep. 1993).

Spielman, R.S., and Ewens, W.J., "A Sibship Test for Linkage in the Presence of Association: The Sib Transmission/Disequilibrium Test," *Am. J. Hum. Genet. 62:*450–458 (Feb. 1998).

Strickland, D.K., et al., "Sequence Identity between the $\alpha_2$–Macroglobulin Receptor and Low Density Lipoprotein Receptor–related Protein Suggests That This Molecule Is a Multifunctional Receptor," *J. Biol. Chem. 265:*17401–17404 (Oct. 1990).

Tanzi, R.E., et al., "Amyloid β Protein Gene: cDNA, mRNA Distribution, and Genetic Linkage Near the Alzheimer Locus," *Science 235:*880–884 (Feb. 1987).

Teschauer, W., et al., "Conditions for Single Strand Conformation Polymorphism (SSCP) Analysis with Broad Applicability: A Study on the Effects of Acrylamide, Buffer and Glycerol Concentrations in SSCP Analysis of Exons of the p53 Gene," *Eur. J. Clin. Chem. Clin. Biochem. 34:*125–131 (Feb. 1996).

Van Gool, D., et al., "α2–Macroglobulin Expression in Neuritic–Type Plaques in Patients With Alzheimer's Disease," *Neurobiol. Aging 14:*233–237 (May/Jun. 1993).

Wu, W.S., et al., "Genetic Studies on Chromosome 12 in Late–Onset Alzheimer Disease," *JAMA 280:*619–622 (Aug. 1998).

Zhang, Z., et al., "Inhibition of $\alpha_2$–macroglobulin/proteinase–mediated degradation of amyloid β peptide by apolipoprotein E and $\alpha_1$–antichymotrypsin: evidence that the $\alpha_2$–macroglobulin/proteinase complex mediates degradation of the Aβ peptide," *Amyloid: Int. J. Exp. Clin. Invest. 3:*156–161 (Sep. 1996).

* cited by examiner

ALPHA-2-MACROGLOBULIN DIAGNOSTIC TEST

RELATED APPLICATIONS

This application claims priority to U.S. Provisional Application No. 60/057,655, filed on Sep. 5, 1997, and U.S. Provisional Application No. 60/093,297, filed on Jul. 17, 1998, the entire contents of which are herein incorporated by reference.

STATEMENT AS TO RIGHTS TO INVENTIONS MADE UNDER FEDERALLY-SPONSORED RESEARCH AND DEVELOPMENT

At least part of the work performed during development of this invention utilized Grant Nos. P50AG05134 and RO1AG12406, from the National Institute of Aging, and Grant No. 5UO1 MH51066, from the National Institute of Mental Health. The U.S. Government has certain rights in this invention.

BACKGROUND OF THE INVENTION

1. Field of the Invention

This invention relates to the area of medical genetics. Specifically, the invention provides a genetic test to identify carriers of specific alleles of the Alpha-2-Macroglobulin gene, the occurrence of which are genetically linked, with high statistical significance, to the condition known as Alzheimer's disease.

2. Related Art

Alpha-2-Macroglobulin ($\alpha_2 M$) is a major serum pan-protease inhibitor which inhibits all four classes of proteases by a unique steric trapping mechanism (Borth, W., *FASEB* 6:3345–3353 (1992)). It is the major representative of a family of plasma proteins, most of which possess a unique internal, cyclic thiol ester bond, referred to as the $\alpha$-macroglobulins (Borth, W., *FASEB* 6:3345–3353 (1992)). Although it functions against a wide variety of human and bacterial endopeptidases (Starkey, P. M. and Barret, A. J., *Proteinases in mammalian cells and tissues*, Barret, A. J. (ed.), North-Holland, N.Y. (pub), pp. 663–696, (1977)), a possible role in pathogenesis is not yet known. In vitro studies have provided a great deal of information regarding protein structure and inhibitory functions (Scottrup-Jensen, L., et al., *J Biol. Chem.* 259:8318–8327 (1984); Feldman, S. R., et al., *Proc. Natl. Acad. Sci. USA* 82:5700–5704, 1985; Kan, C. C., et al., *Proc. Natl. Acad Sci USA* 82:2282–2286 (1985); Bretaudiere, J. P., et al., *Proc. Natl. Acad. Sci. USA* 85:1437–1441 (1988); Van leuven, F., et al., *J Biol. Chem.* 261:11369–11373 (1986)), and at the molecular level, it is known to be part of a related gene cluster on human chromosome 12p (Devriendt, K., et al., *Gene* 81:325–334, 1989) that also includes the $\alpha_2 M$ pseudogene and the pregnancy-zone gene. Recent evidence suggests that $\alpha_2 M$ may be associated with certain morphological characteristics of Alzheimer's Disease (AD).

AD is a neurodegenerative disorder characterized by a global decline in mental function, memory and acquired intellectual skills. It is the most common form of dementia occurring in mid-to late-life and is a major cause of disability and death in the elderly (Price, L. and Sisodia, S., *Annu. Rev. Neurosci.* 21:479–505 (1998)). The appearance of AD in the population according to age is variable, often being categorized into early and late onset forms. In the general population, 40% of the brains of normal individuals show some evidence of $A\beta$ deposits, indicating a subclinical prevalence, and in the population 60 years and older, AD is diagnosed in 10% of the population.

AD is a genetically heterogenous disorder. Early-onset familial AD (EO-FAD) is inherited as an autosomal dominant disorder involving defects in at least three genes, presenilin I (PSENI) on chromosome 14 (Sherrington, R., et al., *Nature* 375:754–760 (1995)), presenilin 2 (PSEN2) on chromosome 1 (Levy-Lehad, E., et al., *Science* 269:973–977 (1995); Rogaev, E. I., et al., *Nature* 376:775–778 (1995)), and $\beta$-amyloid precursor protein (APP) on chromosome 21 (Tanzi, R. E., et al., *Science* 235:880–884 (1987); Goate, A. M., et al., *Nature* 349:704–706 (1991)). These genes account for roughly 30–40% of EO-FAD (Hardy J., *Trends Neurosci.* 20:154–159 (1997); Cruts, M., et al., Hum. Mol. *Genet.* 7.43–51 (1998); Blacker, D. and Tanzi, R. E., *Arch Neurol* 55:294–296 (1998)).

Late-onset AD (LOAD) has been associated with the APOE-$\epsilon$4 allele of apolipoprotein E (APOE) located on chromosome 19 (Strittmatter, W. J., et al., *Proc. Natl. Acad Sci.* (USA) 90:1977–1981 (1993); Saunders, A. M., et al., *Neurology* 43:1467–1472 (1993)). Inheritance of APOE-$\epsilon$4 lowers the age of onset of AD in a dose-dependent manner and is associated with cases of AD occurring from 40 to 90 years. However it has the greatest impact as a risk factor for onset in the 60's (Blacker, D., et al, *Neurology* 48:139–147 (1997); Farrer, L. A., et al., *JAMA* 278:1349–1356 (1997)). More recently, the gene encoding the major neuronal receptor for apoE, the low density lipoprotein receptor-related protein (LRP), located on the long arm of chromosome 12, was shown to be associated with LOAD (Kang, D. E., et al., *Neurology* 49:56–61 (1997)).

Neuropathological hallmarks of AD include abundant neurofibrillary tangles (NFIT), and $\beta$-amyloid deposition in cerebral blood vessels and in senile plaques (SP). Deposited amyloid is composed principally of the 40–42 residue $\beta$-amyloid protein ($A\beta$) (Glenner et al., *Biochem, Biophys Res. Commun.* 120:885–890 (1984)), which is a proteolytic fragment of the $\beta$-amyloid precursor protein (APP) Wang et al., *Nature* 325:733–736 (1987)). Pathogenesis is thought to develop in AD patients when the $A\beta$ protein is organized into neurotoxic fibrils. In vitro studies demonstrate that $A\beta$ is generated as a soluble peptide during cellular metabolism (Haas, C., et al., *Nature* 359:322–325, 1992; Shoji, M., et al., *Science* 258:126–129 (1992)). Several additional plaque-associated proteins are known to promote the in vitro formation of $A\beta$ fibrils, suggesting the possibility that these proteins regulate $A\beta$ aggregation in vivo (Ma, J., et al., *Nature* 372:92–94 (1994); Eriksson, S., et al., *Proc Natl. Acad. Sci. USA* 92:2313–2317 (1995)). Because $A\beta$ deposition likely plays a role in the development of AD, a great deal of research is focused on the synthesis, degradation and clearance of this protein from the affected tissues.

Furthermore, given the potential importance of the APP and $A\beta$ proteins in AD pathogenesis, research is also focused on providing a genetic link between mutations in the APP gene and the occurrence of Alzheimer's disease. Mutations in APP close to or in the $A\beta$ domain are known (Goate et al., *Nature* 349:704–706 (1991); Levy et al., *Science* 248:1124–1126 (1990); Murrell et al., *Science* 254:97–99 (1991); Hendricks et al., *Nature Genet.* 1:218–221 (1992); Chartier-Harlin, M. et al., *Nature* 353:844 (1991); Mullan, M., et al., *Nature Genet.* 1:345 (1992)). In some instances, linkage of the mutation with the occurrence of familial Alzheimer's disease (FAD) was possible.

Also implicated in the development of AD is the possibility that there exists an imbalance between proteases and protease inhibitors which affects normal amyloid metabolism. Antibodies to ubiquitin strongly react with the characteristic amyloid neurofibrillar tangles (Tabaton, M., et al., *Proc. Natl. Acad Sci.* 88:2098–2102 (1991)). The Aβ peptide is generated proteolytically from APP, and proteases cathepsin B and D and protease inhibitors such as protease nexin 1 and α1-antichymotrypsin were found in amyloid plaques (Cataldo, A. M. and Nixon, R. A., *Proc. Natl. Acad Sci.* 87:3861–3865, 1991; Rosenblatt, D. E., et al., *Ann. Neurol* 26:628–634 (1989); Abraham, C. R., et al., *Cell* 52:487–501 (1988)).

Alpha-2-macroglobulin is another protease inhibitor implicated in neural tissue metabolism. Several lines of evidence link the $\alpha_2M$ protein to morphological properties associated with AD patient cerebra. One study in support of a role in neural metabolism identified $\alpha_2M$ as an astroglia-derived neurite-promoting factor for cultured neurons from the rat central nervous system (Mori, T., et al., *Brain Res.* 527:55–61 (1990)). In addition, $\alpha_2M$ has been shown to attenuate the fibrillogenesis and neurotoxicity of Aβ (Hughes, S. R., et al., *Proc. Natl. Acad. Sci.* (USA) 95:3275–3280 (1998); Du, Y., et al., *J Neurochem.* 70:1182–1188 (1998); Zhang, Z., et al., *Amyloid: Int. J Exp. Clin. Invest.* 3:156–161 (1996)). Also suggestive of a connection between $\alpha_2M$ and AD is that $\alpha_2M$ tightly binds the Aβ peptide (Du, Y., et al, *J Neurochem.* 69:299–305 (1997); Hughes, S. R., et al., *Proc. Natl. Acad Sci.* (USA) 95:3275–3280 (1998)), and has been shown to mediate the clearance of Aβ via endocytosis through LRP (Narita, M., et al., *J Neurochem.* 69: 1904–1911 (1997)). Furthermore, two independent studies found that an $\alpha_2M$/protease complex is capable of degrading the Aβ peptide (Zhang, Z., et al., *Amyloid: Int. J. Exp. Clin. Invest.* 3:156–161 (1996); Qiu, W. Q., et al., *J. Biol. Chem.* 271(14):8443–8451 (1996)). In addition, $\alpha_2M$ has been localized to senile plaques (SP) in AD (Bauer, J., et al., *FEBS* 285:111–114 (1991); Van Gool, D., et al., *Neurobiology of Aging* 14:233–237 (1993); Rebeck, G. W., et al., *Ann. Neurol* 37:211–217 (1995)). Van Gool et al., suggest that expression of $\alpha_2M$ could be associated with neurofibrillary changes in senile plaques in AD. (Van Gool, D., et al., *Neurobiology of Aging* 14:233–237 (1993)). An immunocytochemistry study of cerebra of AD patients using two different monoclonal antibodies specific for $\alpha_2M$ found localization in neuritic-type plaques but not preamyloid or burned-out type plaques (Van Gool, D., et al., *Neurobiology of Aging* 14:233–237 (1993)). Because immunoreactivity was associated with microglia in the outer border of the neuritic plaque, Van Gool et al. suggest that $\alpha_2M$ could be a marker for an inflammatory process in the plaques (Van Gool, D., et al., *Neurobiology of Aging* 14:233–237 (1993)).

The human $\alpha_2M$ gene has been cloned and several mutants have been identified. (Poller, W., et al., *Human Genetics* 88:313–319 (1992); Matthijs, G., and Marynen, P., *Nucl. Acids Res.* 19(18):5102 (1991)). One mutation represented a bi-allelic deletion polymorphism in which 5 bases were deleted at positions −7 to −3 of the 5' splice acceptor site of exon 18 (Matthijs, G., and Marynen, P., *Nucl Acids Res.* 19(18):5102 (1991)) (referred to as the A2M-2 allele). The A2M-2 allele, and the wild type A2M allele (referred to as the A2M-1 allele) were found at allele frequencies of 0.18 and 0.82 respectively (Matthijs, G., and Marynen, P., *Nucl. Acids Res.* 19(18):5102 (1991)). The biological consequences of this deletion mutation have not yet been reported, but it is known that exon 18 encodes "exon II" of the bait domain of $\alpha_2M$, which is used to trap proteases.

Another mutation represented a simple polymorphism 25 amino acids downstream from the thiolester site of the protein that interchanges $Val^{1000}$(GTC) and $Ile^{1000}$ (ATC) (Poller, W., et al., *Human Genetics* 88:313–319 (1992) (numbering is based on the cDNA sequence which includes a 24 amino acid signal peptide; this amino acid corresponds to Val/Ile$^{976}$ in the mature protein). The Val, or G allele, and the Ile, or A allele, were found at allele frequencies of 0.30 and 0.70, respectively (Poller, W., et al., *Human Genetics* 88:313–319 (1992)). No difference in $\alpha_2M$ serum levels was associated with the two alleles. This polymorphism is interesting because the mutation occurs near the thiolester active site of the molecule.

Family, twin, and population data all suggest that genes involved in AD remain to be identified (Lautenschlager, N. T., et al., *Neurology* 46(3):641–50 (1996); Bergem, A., et al., *Arch. Gen. Psychiatry* 54:264–270 (1997); Payami, H., et al., *Am J Hum Genet* 60:948–956 (1997)) and several candidates have been reported (for a review, see Hardy J., *Trends Neurosci.* 20:154–159 (1997); Cruts, M., et al., *Hum. Mol. Genet.* 7:43–51 (1998); and Blacker, D., and Tanzi, R. E., *Arch. Neurol.* 55:294–296 (1998)). The identification of specific genes or alleles thereof linked to the development of AD will provide a greater understanding of the mechanisms behind the disease process, a screening method for detection of at-risk individuals, and may lead to effective treatment of this disease. A great deal towards this end has been accomplished already in the study of the APP gene. This invention, linking A2M, and particularly inheritance of the A2M-2 and A2M-G alleles, to the occurrence of Alzheimer's disease, provides another important resource.

SUMMARY OF THE INVENTION

This invention relates to the discovery that particular alleles of A2M are linked to the occurrence of Alzheimer's disease. More specifically, it was found that individuals carrying at least one copy of the A2M-2 allele or who are homozygous for the A2M-G allele are disproportionately represented in a population of AD patients as compared to those unaffected by AD.

Based on this discovery, a diagnostic method was developed that characterizes the A2M genotype of individuals in the population to assess risk for developing AD. In one embodiment of the invention, A2M genotype is determined by isolating nucleic acid from an individual, and analyzing it for the particular A2M alleles of interest. Various embodiments of the invention enable analysis from isolated nucleic acid that is DNA or RNA. In a preferred embodiment, restriction fragment length polymorphism (RFLP) analysis is used to determine A2M genotype.

In a more preferred embodiment of the invention, the nucleic acid is utilized as a template for the amplification of an A2M gene fragment prior to the genotyping analysis. A preferred method is to amplify a fragment that contains the site of the pentanucleotide deletion mutation found in the A2M-2 allele. Analysis of the product of amplification is preferably accomplished by determining the polynucleotide sequence of the amplified fragment. Other methods of analyzing the amplified fragment include size determination, single-strand conformation polymorphism (SSCP) analysis, and RFLP analysis. Another preferred method is to amplify a fragment that encodes amino acid 1000, the residue affected by the mutation found in the A2M-G allele. Analysis of the product of amplification is preferably accomplished by RFLP analysis. Other methods of analyzing the amplified fragment include sequencing or sizing the fragment, and SSCP analysis.

Another embodiment of the invention relates to the use of protein isotyping to assess A2M genotype . In one embodiment, an antibody specific for an $\alpha_2$M variant lacking exon 18 ($\alpha_2$M-2) is used to assess A2M genotype through protein isotyping. In a preferred method of protein isotyping, a second antibody, which is specific for an a $\alpha_2$M protein having exon 18 (the wild type $\alpha_2$M referred to as $\alpha_2$M-1), is used as a control. Yet another embodiment of the invention relates to the use of an antibody specific for the Val$^{1000}$ variant to assess the A2M-G genotype through protein isotyping. In a preferred method of protein isotyping, a second antibody, which is specific for the Ile$^{1000}$ protein, is used as a control. For the protein isotyping methods of the invention, preferably, protein is isolated from an individual and screened with the specific antibodies. More specifically, a more preferred embodiment would utilize Western blot or ELISA technology. In yet another embodiment of the invention an $\alpha_2$M electrophoretic mobility assay is used to detect the $\alpha_2$M-2 variant to assess A2M genotype through protein isotyping.

The invention also relates to diagnostic kits for A2M genotyping. Alternative embodiments of the genotyping kit enable screening of nucleic acid or protein, providing a fast and efficient means for Alzheimer's disease risk assessment.

BRIEF DESCRIPTION OF THE FIGURES

FIG. 1 depicts a map of several chromosome 12 markers. Distances between markers are given in cM. * represents markers used in the traditional linkage analysis techniques described in Example 1 below; @ represents markers used in the analysis described by Pericak-Vance et al. (Pericak-Vance, M. A., et al., *JAMA* 278(15):1237–1241 (1997)); $ represents markers used in both analyses. The letter T inside of a circle represents a telomere of Chromosome 12. The letter C inside of a circle represents the centromere of Chromosome 12.

FIG. 2 depicts the results of a multipoint non-parametric linkage analysis using the program GENEHUNTER (Kruglyak, L., et al., *Am. J Hum. Genet.* 58:1347–1363 (1996)(software available from Kruglyak et al. by anonymous ftp at ftp-genome.wi.mit.edu, or from their World Wide Web site http://www-genome.wi.mit.edu ftp/distribution/software/genehunter)). This was one of several genetic linkage analytic techniques used to determine if there was evidence for linkage in the A2M region, and particularly, whether A2M might be related to recent reports of linkage to the centromeric region of chromosome 12 (Pericak-Vance, M. A., et al., *JAMA* 278(15):1237–1241 (1997)). The results were negative, although there was a weak but non-significant signal in Tier 1. For this analysis, the families from the sample described in Example 1 were divided into "tiers" according to the criteria of Pericak-Vance et al.: Tier 1 (FIG. 2B) is comprised of families in which all affecteds were APOE-ϵ4/ϵ4 (30 families); Tier 2 (FIG. 2C) is comprised of families not in Tier 1 in which all affecteds were APOE-ϵ4 carriers (131 families); Tier 3 (FIG. 2D) is comprised of families in which at least one affected did not carry an APOE-ϵ4 allele (126 families). The analysis was also rum on the total sample (FIG. 2A).

FIG. 3 is a photograph of a 2% agarose gel showing A2M polymorphism genotypes after restriction digestion with MboI. The gel shows a restriction digest pattern with bands representing the G (532 bp fragment) and the A (429 bp fragment) alleles. Genomic DNA isolated from brain tissue and blood was amplified by polymerase chain reaction (PCR) in the presence of oligonucleotide sense primer C23 (SEQ ID NO: 3) and antisense primer AS24 (SEQ ID NO: 4), 10 mM Tris-HCl, 50 mM KCl (pH 8.3), 1.5 mM MgCl$_2$5 mM dNTPs, 5 pmol each primer, and 1.25 U Taq DNA polymerase. The PCR was carried out in a touchdown procedure that stepped down the annealing temperature to increase primer specificity as follows: 1 cycle at 94° C.-5 min; 4 cycles at 94° C.-30 sec, 65° C.-30 sec, 72° C.-1 min; 4cycles at 94° C.-30 sec, 62° C.-30 sec, 72° C.-1 min; 4 cycles at 94° C.-30 sec, 59° C.-30 sec, 72° C.-1 min; 20 cycles at 94° C.-30 sec, 56° C.-30 sec, 72° C.-1 min; and 1 cycle at 72° C.-5 min. For each reaction mixture, 10 units of MboI were added to the amplified product of 615 bps and digestion carried out at 37° C. for 3 hours, producing fragments of 532 and 429 bps. The digested product was loaded onto a 2% agarose gel treated with ethidium bromide (0.005%) and electrophoresed for 2 hours under constant voltage (150V), which is sufficient to separate the digested product so that the 532 and 429 bp bands can be distinguished. After electrophoresis, DNA fragments were visualized by UV illumination using a Biorad Geldoc system. Incomplete digestion was monitored by looking for the presence of the 615 bp fragment.

DETAILED DESCRIPTION OF THE PREFERRED EMBODIMENTS

Definitions

Figure 1:
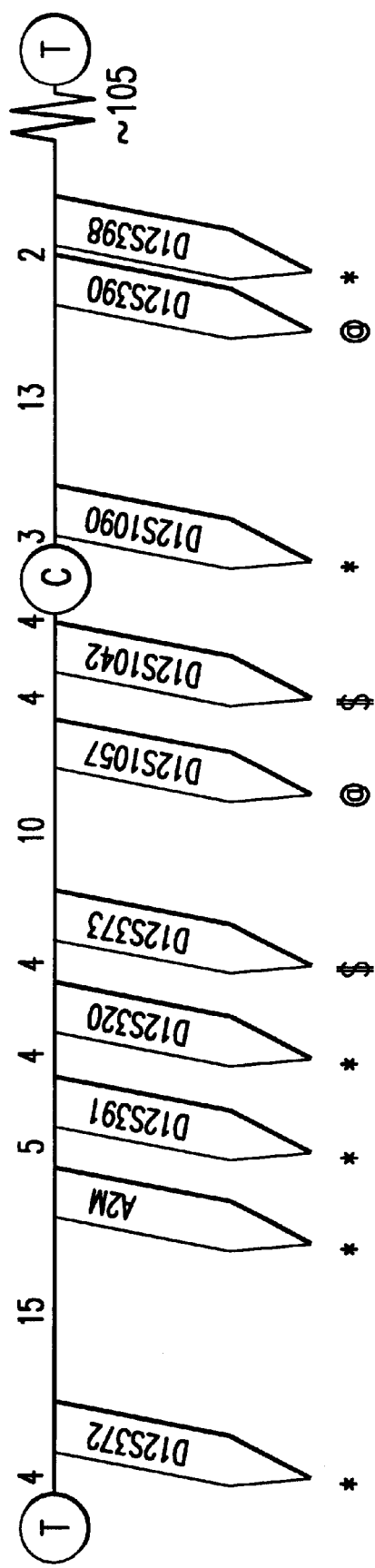
FIG. 1 Map of Chromosome 12 Markers.
Figure 2A:
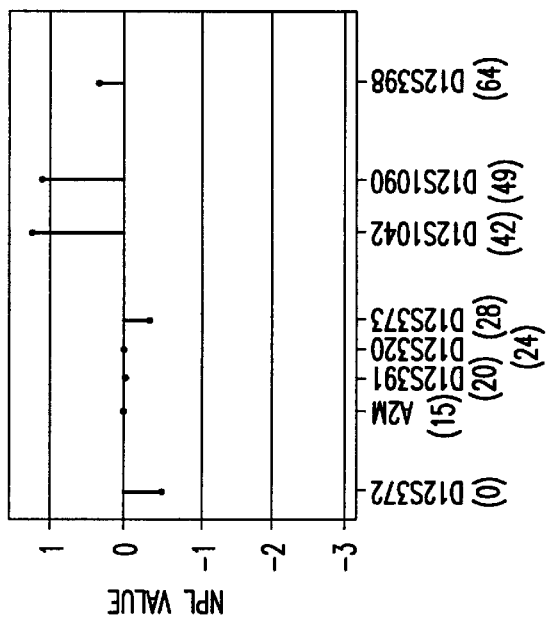
FIGS. 2A–2D Results of Multipoint Non Parametric Linkage Analysis of Chromosome 12 Markers to Alzheimer's Disease.
Figure 2B:
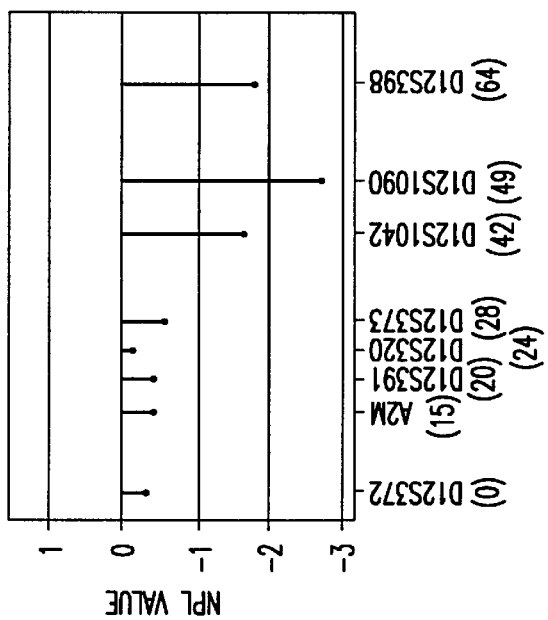
Figure 2C:
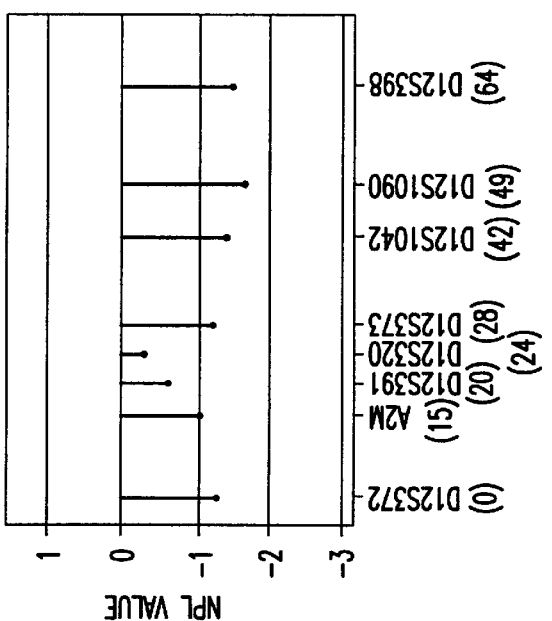
Figure 2D:

In the description that follows, a number of terms used in recombinant DNA technology are extensively utilized. In order to provide a clearer and consistent understanding of the specification and claims, including the scope to be given such terms, the following definitions are provided.

Polymorphic: As is understood by one of ordinary skill in the art, a nucleic acid molecule is said to be "polymorphic" if it may exist in more than one form. For example, a nucleic acid molecule is said to be polymorphic if it may have more than one specific nucleotide sequence (such as degenerate nucleic acid molecules or genes that may each encode the same protein). More commonly, a nucleic acid molecule is said to be polymorphic if it displays size differences (i. e., differences in length), particularly when comparisons of nucleic acid molecules from different individuals are made. Of course, other definitions of the term "polymorphic" will be apparent to one of ordinary skill and are also encompassed within this definition.

Primer: As used herein "primer" refers to a single-stranded oligonucleotide that is extended by covalent bonding of nucleotide monomers during amplification or polymerization of a DNA molecule. Minisatellite primers used for the amplification of minisatellite dimer, trimer, tetramer, etc., sequences are well-known in the art.

Restriction Fragment Length Polymorphism (RFLP): As used herein, a restriction fragment polymorphism refers to a polymorphism in the length of restriction fragments produced by digestion of DNA by a particular restriction endonuclease. The genomic DNA of two individuals in a population will differ in sequence at many sites. When these differences occur in the recognition site for a restriction endonuclease, then a polymorphism in the length of restriction fragments produced by digestion of the DNA of the two individuals will result.

Single-Strand Conformation Polymorphism (SSCP): As used herein, a single-strand conformation polymorphism refers to a structural variation in single-stranded DNA due to sequence-dependent intrastrand secondary structure. Secondary structure is determined by the balance between destabilizing thermal forces and weak stabilizing forces. These forces are in turn dependent on the primary structure of the DNA strand, allowing a sequence variation as small as a single base point mutation to lead to structural variations between otherwise identical sequences.

The differences in secondary structure among variants allow the detection of SSCPs by electrophoresis using non-denaturing gels. Under the appropriate conditions, the electrophoretic mobility of the DNA is dependent not only on its length and molecular weight, but also on its conformation. Thus, not only will complementary strands migrate as separate bands on a gel, but small differences in sequence will also alter the mobility of these strands.

Template: The term "template" as used herein refers to a double-stranded or single-stranded nucleic acid molecule which is to be amplified, synthesized or sequenced. In the case of a double-stranded DNA molecule, denaturation of its strands to form a first and a second strand is performed before these molecules may be amplified, synthesized or sequenced. A primer, complementary to a portion of a DNA template is hybridized under appropriate conditions and the DNA polymerase of the invention may then synthesize a DNA molecule complementary to said template or a portion thereof. The newly synthesized DNA molecule, according to the invention, may be equal or shorter in length than the original DNA template. Mismatch incorporation or strand slippage during the synthesis or extension of the newly synthesized DNA molecule may result in one or a number of mismatched base pairs. Thus, the synthesized DNA molecule need not be exactly complementary to the DNA template.

Incorporating: The term "incorporating" as used herein means becoming a part of a DNA molecule or primer.

Amplification: As used herein "amplification" refers to any in vitro method for increasing the number of copies of a nucleotide sequence with the use of a DNA polymerase. Nucleic acid amplification results in the incorporation of nucleotides into a DNA or molecule or primer thereby forming a new DNA molecule complementary to a DNA template. The formed DNA molecule and its template can be used as templates to synthesize additional DNA molecules. As used herein, one amplification reaction may consist of many rounds of DNA replication. DNA amplification reactions include, for example, polymerase chain reactions (PCR). One PCR reaction may consist of 5 to 100 "cycles" of denaturation and synthesis of a DNA molecule.

Oligonucleotide: "Oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

Nucleotide: As used herein "nucleotide" refers to a base-sugar-phosphate combination. Nucleotides are monomeric units of a nucleic acid sequence (DNA and RNA). The term nucleotide includes deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Thermostable: As used herein "thermostable" refers to a DNA polymerase which is resistant to inactivation by heat. DNA polymerases synthesize the formation of a DNA molecule complementary to a single-stranded DNA template by extending a primer in the 5'-to-3' direction. This activity for mesophilic DNA polymerases may be inactivated by heat treatment. For example, T5 DNA polymerase activity is totally inactivated by exposing the enzyme to a temperature of 90° C. for 30 seconds. As used herein, a thermostable DNA polymerase activity is more resistant to heat inactivation than a mesophilic DNA polymerase. However, a thermostable DNA polymerase does not mean to refer to an enzyme which is totally resistant to heat inactivation and thus heat treatment may reduce the DNA polymerase activity to some extent. A thermostable DNA polymerase typically will also have a higher optimum temperature than mesophilic DNA polymerases.

Hybridization: The terms "hybridization" and "hybridizing" refer to the pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used. In the present invention, the term "hybridization" refers particularly to hybridization of an oligonucleotide to a DNA template molecule.

Other terms used in the fields of recombinant DNA technology and molecular and cell biology as used herein will be generally understood by one of ordinary skill in the applicable arts.

This invention relates to the finding that particular genotypes of the A2M locus may be linked to the occurrence of Alzheimer's disease. More specifically, it was found that individuals carrying at least one copy of the A2M-2 allele or who are homozygous for the A2M-G allele are more highly represented in AD patients than in the population as a whole.

Therefore, a first embodiment of the invention is to utilize A2M genotyping as a diagnostic method for determining risk-assessment for the onset of AD. To that end, cells, tissues, organs or other samples from an individual are obtained in order to isolate nucleic acid or protein. Preparation of the nucleic acid is done by methods that are well-known in the art (See, e.g., Maniatis, T., et al., *Molecular Cloning: A Laboratory Manual*, Cold Spring Harbor, N.Y.: Cold Spring Harbor Laboratory Press (1989); Kauffman, P. B., et al., *Handbook of Molecular and Cellular Methods in Biology and Medicine*, Boca Raton, Florida: CRC Press (1995)). In one embodiment of the invention, the nucleic acid isolated is DNA. In another embodiment the nucleic acid is RNA, which is subsequently converted to complimentary DNA (cDNA) prior to processing and analysis by means of reverse transcription using procedures well known in the art (see, e.g., Unit 5.5 in Ausubel, F. M. et al., eds., *Current Protocols in Molecular Biology*: John Wiley and Sons, Inc. (1997)). The nucleic acid samples thus prepared can be analyzed to determine the A2M genotype.

In a preferred embodiment of the invention, the sample(s) is genotyped for the A2M-2 allele. In another preferred embodiment of the invention, the sample(s) is genotyped for the A2M-G allele.

In one embodiment of the invention, the genotype analysis is done utilizing RFLP analysis. RFLP analysis is a procedure well known in the art for identifying polymorphisms in DNA. After restriction endonuclease digestion with one or more restriction enzymes, the DNA sample(s) is analyzed for a polymorphic variation. This step is usually accomplished by separation of the DNA fragments by size, a procedure which permits the determination of the presence of unique polymorphic fragments in one or more of the DNA samples. The fragments may be separated by any physical or biochemical means including gel electrophoresis, capillary electrophoresis, chromatography (including sizing, affinity and immunochromatography), density gradient centrifugation and imnunoadsorption. For carrying out the present invention, separation of DNA fragments by gel electrophoresis is particularly preferred, as it provides a rapid and highly reproducible means of sensitive separation of a multitude of DNA fragments, and permits direct, simultaneous comparison of the fragments in several samples of DNA, or samples of DNA from a first and a second individual.

Gel electrophoresis is typically performed on agarose or polyacrylamide gels according to standard protocols. Samples are loaded onto the gels, usually with samples containing DNA fragments prepared from different sources of genomic DNA being loaded into adjacent lanes of the gel to facilitate subsequent comparison. Reference markers of known sizes may be used to facilitate the comparison of samples. Following electrophoretic separation, DNA fragments may be visualized and identified by a variety of techniques that are routine to those of ordinary skill in the art, such as ethidium bromide staining or autoradiography. One can then examine the samples for identifying polymorphic fragment patterns or for the presence of one or more unique bands.

A preferred embodiment of the invention is to utilize a restriction endonuclease specific for a restriction site created or deleted due to the mutation (substituting G for A) found in the A2M-G allele, and size fractionation by agarose or polyacrylamide gel electrophoresis to test for the occurrence of the A2M-G allele. A more preferred embodiment utilizes the restriction enzyme MboI for RFLP analysis to test for the occurrence of the A2M-G allele.

Another preferred embodiment of the invention is to analyze the sample for the occurrence of the A2M-2 allele by digestion with a restriction endonuclease specific for a restriction site that has been created or deleted due to the pentanucleotide deletion found in the A2M-2 allele, followed by size fractionation by agarose or polyacrylamide gel electrophoresis. One of ordinary skill in the art will be able to select an appropriate restriction endonuclease(s) for use in RFLP analysis by analyzing the site of the A2M-2 pentanucleotide deletion. This can be done by determining whether the A2M-2 allele contains a restriction site not found in the wild type A2M allele (A2M-1), or whether a restriction site found in the A2M-1 allele in the region of the deletion mutation has been lost. Restriction sites for commercially available restriction endonucleases are described in Table 3.1.1 in Ausubel, F. M. et al., eds., *Current Protocols in Molecular Biology*: John Wiley and Sons, Inc. (1997).

In a preferred embodiment of the invention, the DNA is amplified prior to the genotyping analysis. General methods for amplification and analysis of the DNA fragments are well-known to one of ordinary skill in the art (see, e.g., U.S. Pat. Nos. 4,683,195; 4,683,202; and 4,800,159; Innis, M. A., et al., eds., PCR *Protocols: A Guide to Methods and Applications*, San Diego, Calif.: Academic Press, Inc. (1990); Griffin, H. G., Griffin, A. M., eds., *PCR Technology: Current Innovations*, Boca Raton, Fla.: CRC Press (1994) and Ausubel, F. M. et al, eds., Chapter 15 in *Current Protocols in Molecular Biology*: John Wiley and Sons, Inc. (1997)). Typically, these methods comprise contacting the DNA sample with a thermostable DNA polymerase in the presence of one or more primer sequences and amplifying the DNA sample to generate a collection of amplified DNA fragments, preferably by PCR or an equivalent automated amplification technique.

Based on the sequence of the alleles provided herein, PCR primers are constructed that are complementary to either (1) the region of A2M encompassing the site for the pentanucleotide deletion found in the A2M-2 allele, or (2) the region of A2M encompassing amino acid 1000 of the $\alpha_2$M protein. A primer consists of a consecutive sequence of polynucleotides complementary to any region in the allele encompassing the position of interest. The size of these PCR primers range anywhere from five bases to hundreds of bases. However, the preferred size of a primer is in the range from 10 to 40 bases, most preferably from 15 to 32 bases. As the size of the primer decreases so does the specificity of the primer for the targeted region. Hence, even though a primer which is less than five bases long will bind to the targeted region, it also has an increased chance of binding to other regions of the template polynucleotide which are not in the targeted region. Conversely, a larger primer provides for greater specificity, however, it becomes quite cumbersome to make and manipulate a very large fragment. Nevertheless, when necessary, large fragments are employed in the method of the present invention.

A more preferred method of the invention for amplifying the DNA is to utilize primers that flank the site of the pentanucleotide deletion mutation present in the A2M-2 allele and provide a product that contains the sequence encoding exon 18 of $\alpha_2$M. More preferably, the invention utilizes primer 5' CTT TCC TTG ATG ACC CAA GCG CC 3' (SEQ ID NO: 1) and primer 5' GTT GAA AAT AGT CAG CGA CCT C 3' (SEQ ID NO: 2) (Matthijs, G., and Marynen, P., *Nucl Acids Res.* 19(18):5102 (1991)) during the amplification step.

Another preferred method of the invention for amplifying the DNA is to utilize primers that flank the sequence encoding amino acid 1000 of the $\alpha_2$M protein and provide a product that contains the sequence encoding said amino acid. More preferably, the invention utilizes the sense primer C23: 5' ATC CCT GAA ACT GCC ACC AA 3' (SEQ ID NO: 3) and antisense primer AS24: 5' GTA ACT GAA ACC TAC TGG AA 3' (SEQ ID NO: 4) during the amplification step.

Following amplification by the methods of the present invention, the amplified DNA fragments may be analyzed to identify a specific polymorphism. The analysis can be done by determining the polynucleotide sequence of the amplified fragments using procedures well known in the art. Several methods of sequencing DNA are described by Ausubel, F. M. et al., eds., in Chapter 7 in *Current Protocols in Molecular Biology*: John Wiley and Sons, Inc. (1997) (see also, U.S. Pat. Nos. 4,962,022 and 5,498,523, which are directed to methods of DNA sequencing). This method of analysis is preferred when the amplified fragment contains the site of the deletion mutation found in the A2M-2 allele.

In another embodiment, the analysis can be done by RFLP analysis, as was previously described herein. This method of analysis is preferred when the fragment amplified encodes amino acid 1000 of the $\alpha_2$M protein.

In yet another embodiment, analysis of the amplified sample can be done by Single-Strand conformation polymorphism (SSCP) analysis. SSCP analysis is a procedure well known in the art for identifying polymorphisms in DNA (see, e.g., Orita, M., et al., *Proc. Natl. Acad Sci.* USA 86:2766–2770 (1989); Teschauer, W., et al., *Eur. J Clin. Chem. Clin. Biochem.* 34:125–131 (1996); and Paccoud, B., et al., *Nucl. Acids Res.* 26(9):2245–2246 (1998)). After denaturation of a double stranded DNA sample(s), the single stranded DNA is analyzed for a polymorphic variation. This step is usually accomplished by separation of the single stranded DNA using electrophoresis, a procedure which permits the determination of the presence of unique polymorphic conformations in the DNA sample(s). The strands may be separated on a non-denaturing polyacrylamide gel. Gel electrophoresis and visualization of the DNA may be performed as described immediately herein.

In an additional embodiment, the amplified sample can be analyzed directly by size fractionation if the sequence of interest contains an insertion or deletion relative to the control DNA.

An alternative embodiment of the invention utilizes protein isotyping to determine the A2M genotype. The $\alpha_2M$ variant found in the A2M-2 genotype is predicted to lack exon 18 due to the loss of nucleotides in the splice acceptor site of exon 18. These nucleotides are believed to be necessary for effective splicing of $\alpha_2M$. In the A2M-G genotype, $Ile^{1000}$ (ATC) is replaced by $Val^{1000}$(GTC). Antibodies specific to each of these variant forms of $\alpha_2M$ can be utilized to screen individuals for the occurrence of these variants and thus for the occurrence of the A2M-2 or A2M-G alleles.

The term "antibody" refers both to monoclonal antibodies which have a substantially homogeneous population and to polyclonal antibodies which have heterogeneous populations. Polyclonal antibodies are derived from the antisera of immunized animals, and monoclonal antibodies to specific $\alpha_2M$ variants may be obtained by methods known in the art (Kohler and Milstein, *Nature* 256:495–497, 1975). Such antibodies may be of any immunoglobulin class including IgG, IgM, IgE, IgA, IgD and any subclass thereof. The term "antibody" is meant to include both intact molecules as well as fragments thereof, such as Fab and F(ab')$_2$, which are capable of binding antigen. The antibodies are tested for their ability to distinguish the $\alpha_2M$-2 from the $\alpha_2M$-1 proteins, or the $Val^{1000}$ from the $Ile^{1000}$ proteins by a standard immunoassay method such as ELISA (Chapter 11 in *Current Protocols In Molecular Biology*: Green Publishing Associates and Wiley-Interscience (1991)), using recombinantly expressed $\alpha_2M$.

Once tested, the antibodies may be used to detect the presence of the $\alpha_2M$-2variant or the $\alpha_2M$ $Val^{1000}$ variant. These antibodies may be used in immunoassay techniques well known in the relevant arts, such as Western Blot or ELISA. Thus, in one embodiment, an antibody specific for the $\alpha_2M$-2 variant is used to assess A2M genotype through protein isotyping. In a preferred method of protein isotyping, a second antibody, which is specific for $\alpha_2M$-1 is used as a control. Yet another embodiment of the invention relates to the use of an antibody specific for the $Val^{1000}$ variant to assess the A2M-G genotype through protein isotyping. In a preferred method of protein isotyping, a second antibody, which is specific for the $Ile^{1000}$ protein, is used as a control. For the protein isotyping methods of the invention, preferably, protein is isolated from an individual and screened with the specific antibodies.

An alternative method of protein isotyping the A2M-2 genotype is to assay for the $\alpha_2M$-2 variant using an $\alpha_2M$ electrophoretic-mobility assay, which consists of analyzing the electrophoretic mobility of $\alpha_2M$ under non-denaturing conditions after incubation with a protease, or other reagent capable of converting $\alpha_2M$ to the fast form (Barret, A. J., et al., *Biochem. J.* 181: 401–418 (1979); Bowen, M. E., and Gettins, P. W., *J. Biol Chem.* 273:1825–1831 (1998)). $\alpha_2M$ can exist in two forms easily distinguishable by mobility in gel electrophoresis (Barret, A. J., et al., *Biochem. J.* 181: 401–418 (1979)). The difference in mobility is due to a conformational change. $\alpha_2M$ has a tetrameric structure that undergoes a conformational change upon proteolytic cleavage near the center of the bait domain by a protease (Borth, W. *FASEB* 6: 3345–3353 (1992)). This conformational change traps the protease ((Borth, W. *FASEB* 6: 3345–3353 (1992))), and results in an increase in electrophoretic mobility on poly-acrylamide gels run under non-denaturing conditions (this form is referred to as the "fast form" of $\alpha_2M$) (Barret, A. J., et al., *Biochem. J.* 181: 401–418 (1979); Bowen, M. E., and Gettins, P. W., *J. Biol Chem.* 273:1825–1831 (1998)). This "slow to fast" conversion is used as the basis for an assay for this conformational change, and the two different $\alpha_2M$ conformations are referred to as the slow and fast forms (Bowen, M. E., and Gettins, P. W., *J. Biol Chem.* 273:1825–1831 (1998)). This assay is referred to herein as the $\alpha_2M$ electrophoretic mobility assay.

Because the $\alpha_2M$-2 variant is expected to lack exon 18, the second of the two exons of the bait domain, it is also expected that this variant would be unable to undergo the conformational change that increases electrophoretic mobility converting it from the slow form to the fast form of $\alpha_2M$. Thus, the $\alpha_2M$-2 variant can be identified using the $\alpha_2M$ electrophoretic mobility assay.

The $\alpha_2M$ electrophoretic mobility assay and methods of purifying $\alpha_2M$ from serum are described by Barret et al. in Barret, A. J., et al., *Biochem. J.* 181: 401–418 (1979), and by Bowen et al. in Bowen, M. E., et al., *Arch. Biochem. Biophys.* 337:191–201 (1997), and in Bowen, M. E., and Gettins, P. W., *J. Biol. Chem.* 273:1825–1831 (1998). Reagents for use in the conversion of $\alpha_2M$ to the fast form include proteases, such as trypsin, papain, thermolysin or chymotrypsin; ammonia or low-molecular-weight ammonium analogues, such as $(NH_4)_2SO_4$, methylammonium chloride and ethylammonium chloride; and salts of certain amines such as 1,3-diaminopropane, ethanolamine and methylamine (Bowen, M. E., and Gettins, P. W., *J. Biol. Chem.* 273:1825–1831(1998)). After incubation with one of these reagents, preferably a protease, the $\alpha_2M$ sample may be run on polyacrylamide gel under nondenaturing conditions, such as those described in Bowen, M. E., et al., *Arch. Biochem. Biophys.* 337:191–201 (1997). The $\alpha_2M$ sample may be detected by methods well known in the art such as by radio labelling the protease used, or by Western Blot using anti-$\alpha_2M$ antibodies. The $\alpha_2M$-2 variant, and/or the fast form of $\alpha_2M$-l may be used as controls for comparison of electrophoretic mobility with the sample being analyzed.

The invention also provides kits for use in the identification, analysis and typing of polymorphic DNA according to the present methods. Kits according to the present invention may comprise a carrying means being compartmentalized to receive in close confinement therein one or more containers such as vials, tubes, bottles and the like. Each of such containers may comprise components or a mixture of components needed to perform genotyping analysis.

A kit for genotyping DNA can comprise a number of containers. In one example of such a kit, a first such container can contain a substantially purified sample of the primers with the sequences of SEQ ID NOs 1 and 2 described above. A second such container can contain a $\alpha_2M$-2 DNA. A third such container may contain $\alpha_2M$-1 DNA. In another example of a kit for genotyping DNA, a first such container can contain a substantially purified sample of the primers with the sequences of SEQ ID NOs 3 and 4 described above. A second such container can contain $\alpha_2$M Val$^{1000}$ DNA. A third such container may contain $\alpha_2$M Ile$^{1000}$ DNA.

In another embodiment, the invention provides a kit for A2M genotyping by means of protein isotyping. Such a kit can include one or more containers. In an example of such a kit, a first such container may contain an antibody specific to the $\alpha_2$M-2 protein. A second such container may contain an antibody specific to the $\alpha_2$M-1 protein. A third such container may contain a substantially purified sample of the a $\alpha_2$M-2 variant, or fragment thereof. A fourth such container may contain a substantially purified sample of $\alpha_2$M-1 protein, or fragment thereof. In another example of a kit for A2M genotyping by means of protein isotyping, a first such container may contain an antibody specific to the $\alpha_2$M Val$^{1000}$ variant. A second such container may contain an antibody specific to $\alpha_2$M Ile$^{1000}$ protein. A third such container may contain a substantially purified sample of the $\alpha_2$M Val$^{1000}$ variant, or fragment thereof. A fourth such container may contain a substantially purified sample of $\alpha_2$M Ile$^{1000}$ protein, or fragment thereof. In yet another example of a kit for A2M genotyping by means of protein isotyping, a first container may contain a protease or other reagent for use in conversion of an $\alpha_2$M to the fast form. A second such container may contain a substantially purified sample of the $\alpha_2$M-2 variant. A third such container may contain a substantially purified sample of the fast form of $\alpha_2$M-1. Other containers may contain reagents for use in the purification of $\alpha_2$M or for use in electrophoresis.

It will be readily apparent to those skilled in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

To identify novel AD genes, the inventors employed a candidate gene strategy focusing on genes for known LRP ligands other than apoE and APP (Kounnas, M., et al., *Cell* 82:331–340 (1995)). $\alpha_2$M is a major LRP ligand and major serum pan-protease inhibitor which inhibits all four classes of proteases (Borth, W., *FASEB* 6:3345–3353 (1992)). In brain, A2M is upregulated during injury along with its major receptor, the low density lipoprotein receptor-related protein (LRP) (Strickland, D. K., et al., *J. Biol Chem.* 265:17401–17404(1990); Businaro, R., et al., *Exp. Brain Res.* 88:213–218 (1992); Lopes, M. B., et al., *FEBS Lett.* 338:301–305 (1993)). $\alpha_2$M has been localized to senile plaques (SP) in AD (Bauer, J., et al., *FEBS* 285:111–114 (1991)) and tightly binds the βAP peptide, the major component of β-amyloid in SP and cerebral blood vessel deposits (Du, Y., et al, *J. Neurochem.* 69:299–305 (1997) and Hughes, S. R., et al., *Proc. Natl. Acad. Sci.* (USA) 95:3275–3280 (1998)). $\alpha_2$M has also been shown to attenuate the fibrillogenesis and neurotoxicity of βAP (Hughes, S. R., et al., *Proc. Natl. Acad. Sci.* (USA) 95:3275–3280 (1998) and Du, Y., et al., *J. Neurochem.* 70:1182–1188 (1998)) and to mediate both its degradation (Qiu et al., *J. Biol Chem.* 271:8443–8451 (1996)) and clearance via endocytosis through LRP (Narita, M., et al., *J. Neurochem.* 69:1904–1911 (1997)). In view of these findings implicating $\alpha_2$M in AD, the inventors tested for a genetic association between A2M and AD.

During the course of this study, chromosome 12 linkage to AD was reported as part of a genome scan (Pericak-Vance, M. A., et al., *JAMA* 278(15):1237–1241 (1997)). Since A2M maps within 30 cM of the implicated chromosome 12 markers (Krauter, K., et al., *Nature* 377:321–333 (1995)), the inventors attempted to confirm this result using the National Institute of Mental Health (1I1I) Genetics Initiative AD sample (Blacker, D., et al, *Neurology* 48:139–147 (1997)) and to determine whether a genetic association of A2M with AD may account for the previously published chromosome 12 linkage.

Example 1

Pentanucleotide Deletion Allele

A. Methods

1. Sample

To test for a link between A2M and AD, the inventors used the National Institute of Mental Health (NIMH) Genetics Initiative AD sample, a large sample of affected sibling pairs and other small families with AD (Blacker, D., et al., in *Neurology* 48:139–147 (1997)). Participants were recruited from local memory disorder clinics, nursing homes, and the surrounding communities with the only requirement for inclusion in the sample being that each family include at least two living blood relatives with memory problems. They were evaluated following a standardized protocol (Blacker, D., et al., *Arch. Neurol.* 51:1198–1204 (1994)) to assure that they met NINCDS/ADRDA criteria for Probable AD (or in the case of secondary probands, Possible AD) (McKhann, G., et al., *Neurology* 34:939–944 (1984)), or research pathological criteria for Definite AD (Khachaturian, Z., *Arch. Neurol.* 42:1105 (1985)). Among the affected individuals, 142(22.2%) had autopsy confirmation of the diagnosis of AD. Unaffected relatives, generally siblings, were included when they were available and willing to participate.

There were a total of 239 unaffected subjects from 131 families (45.6%). An additional 22 study subjects with blood available who had unclear phenotypes were considered phenotype unknown, as were 5 unaffected subjects with unknown ages, and 19 unaffected subjects below 50 years of age (primarily children of affected participants). There were a total of 639 individuals affected with AD, from 286 families. The majority of the affected individuals were sibling pairs (202 families, 71%), but there were 46 larger sibships (16%), and 38 families with other structures (13%; e.g., parent-child, first cousin, avuncular, extended). All subjects (or, for significantly cognitively impaired individuals, their legal guardian or care-giver with power of attorney) gave informed consent.

The full sample was used in the descriptive statistics for genotype counts and allele frequencies, for the analyses of age of onset in affected individuals, and for all of the genetic linkage analyses (except ASPEX, which uses sibships only). However, because the Mantel-Haenzel test, conditional logistic regression, and Sibship Disequilibrium Test depend on comparisons of closely related affected and unaffected individuals, these were performed on a subsample including all families in which there was at least one affected and at least one unaffected sibling with A2M data available: 104 families with 217 affected and 181 unaffected siblings.

In order to avoid examining very early onset AD, which appears to have a distinct genetic etiology (Blacker, D., & Tanzi, R. E., *Arch Neurol* 55:294–296 (1998)), only those families in which all examined affected individuals experienced the onset of AD at age 50 or later were included. Although LOAD is conventionally identified based on onset after age 60, families with onsets between 50 and 60 were included because onset in this decade is only partly explained by the known AD genes. Age of onset was determined based on an interview with a knowledgeable informant and review of medical records.

2. Amplification and Genotyping of A2M, APOE, and Chromosome 12 Markers

The A2M exon 18 splice acceptor pentanucleotide deletion (the A2M-2 allele) was manually genotyped according to the protocol described in Matthijs et al. (Matthijs, G., & Marynen, P., *Nuc. Acid Res.* 19:5102 (1991)). A 326 bp fragment was amplified by PCR using primers having the sequences described in SEQ ID NOs 1 and 2. The amplified fragment was then sequenced using 33P in a 96-well format on 6% denaturing polyacrylamide gels. The presence of the deletion resulted in a 5 bp smaller amplicon. APOE was genotyped as described in Blacker et al. (Blacker, D., et al., *Neurology* 48:139–147 (1997)). Chromosome 12 markers were genotyped using primers that were either provided from the Weber 8 set (Research Genetics) or were custom synthesized (BRL).

Manual genotyping was carried out using a 96-well microtiter dish format. Three to 10 nanograms, of human DNA was mixed with a reaction buffer, deoxynucleotide mix (e.g. for a poly-[dGdT] STR, the final concentration is 200 mM each of dATP, dCTP and dTTP; and 2 mM dGTP), I mCi alpha-32PdGTP or 33P-dGTP, 15 pM of each flanking primer and 0.25 units of Taq polymerase in a total volume of 10 ml. The reactions were denatured at 94° C. for 4 min, followed by 25–30 cycles of 1 min denaturing at 94° C., 0.5–1 min annealing (variable temperature, usually 55–65 ° C.) and extension for 1 min at 72° C. Fourty-eight (48) experimental and two control (for standardization of size) samples were loaded on a gel at one time, thereby increasing the amount of information per gel. Whenever possible (e.g., if marker background was sufficiently low) multiple markers (two to four markers) were multiplexed, or were temporally staggered (30–45 minutes) two to three mm on a single gel. Allele sizes for CEPH individuals 1331-01 and 1331-02 were used as standards. In the rare event that no standards were available for a marker, an initial gel was run which included a sequencing ladder to determine allele sizes in these individuals. Two $\mu$ls of sample were mixed with loading dye and size-fractionated on a 6% denaturing polyacrylamide gel. The gels were then dried and placed on X-ray film for 2–24 hrs. at −80° C. and read by two independent readers.

3. Overview of Statistical Techniques

Five groups of statistical analyses were used to explore the relationship between A2M and AD in study families. First, the inventors sought to describe the sample by A2M genotype, and calculated allele frequencies for affected and unaffected individuals. Second, stratified on families, Mantel-Haenzel odds ratios were calculated for the effect of possessing an A2M-2 allele on risk for AD, and conditional logistic regression, conditioning on family, was used to control for the effect of APOE-$\epsilon$4. Third, association was tested for using the Sibship Disequilibrium Test (SDT), a variation of the Transmission Disequilibrium Test (TDT) that is able to detect linkage and association in the absence of parental data. Fourth, a variety of techniques were used to assess whether any A2M effect occurs via a change in age of onset. Fifth, several genetic linkage methods were used to assess the relationship between A2M and AD, and whether any association might be related to the recent report of linkage to centromeric markers on chromosome 12. Wherever possible, APOE-$\epsilon$4 effects were controlled for by stratification or by including APOE-$\epsilon$4 as a covariate in muliivariate analyses. Except as otherwise noted, the analyses reported here were performed in the SAS statistical analysis package (SAS Institute, SAS Program Guide, Version 6, Cary, NC (1989)).

For all types of analysis, allele frequencies were computed from the data, but rare alleles were adjusted up to a frequency of 0.01 (with a compensatory small decrease in the frequency of the most common alleles) in order to minimize the possibility of a false positive result. All analyses were repeated using the uncorrected frequencies.

B. Results

1. Genotype and Allele Frequencies

For descriptive purposes, A2M genotype counts and allele frequencies were examined in affected and unaffected subjects in study families. Unaffected individuals in AD families are not genetically independent of their affected relatives, of course, and thus would be expected to show higher frequencies of AD-associated alleles compared to the general population. However, given an increased risk of AD with a given allele, its frequency would be expected to be higher among affected individuals than among their unaffected relatives. However, since these frequencies are pooled across families, they are neither as accurate nor as powerful an indicator of genetic association as the SDT.

A2M genotype counts and allele frequencies for A2M-2 are reported separately for primary and secondary probands, with primary probands serving as the primary subject population, and secondary probands as a confirmation sample. Allele frequencies in the probands were compared to those for unaffected individuals based on the oldest unaffected individual from each of the 105 families in which one or more unaffected subjects with A2M data was available. In addition, the analyses were repeated using an unaffected sample that had passed through a majority of the age of risk, the "stringent" unaffecteds, those who were at least as old as the age of onset of the latest-onsetting affected family member, again selecting the oldest such individual in each family. Because age of onset is correlated in families (Farrer, L. A., et al., *Neurology* 40:395–403 (1990)), using onset ages in the subjects' own families is preferable to setting an arbitrary cutoff.

The applicants initially determined genotype counts and allele frequencies for the bi-allelic 5' exon 18 splice acceptor deletion polymorphism in A2M (Matthijs, G., Marynen, P., *Nuc. Acid. Res.* 19:5102 (1991)) in primary probands, secondary probands, unaffected individuals (oldest in family), and "stringent" unaffecteds, (those who have reached the onset age of the latest-onsetting affected, again using the oldest such individual), stratified on individual APOE dose (see Tables 1 and 2). The combined genotype frequencies for the possession of 1 or 2 A2M-2 alleles was higher in the primary and secondary probands (29.5% and 31.9%) than in the oldest unaffecteds (22.9%) and oldest stringent unaffected (19.3 %; Table 1). The A2M-2 allele frequencies for primary and secondary probands; were similar (16.4% and 17.7%) and both were lower than those observed in unaffecteds individuals (12.9% for oldest unaffecteds and 10.5% for oldest stringent unaffecteds; Table 2). The effect was particularly marked among the APOE-$\epsilon$4 zero-dose individuals (15.0% for primary probands and 19.4% for secondary probands vs. 4.3% for oldest unaffecteds and 3.7% for oldest stringent unaffected).

TABLE 1

A2M Genotypes Stratified on Individual APOE-ε4 Dose

| | Primary Probands | | | Secondary Probands | | | Oldest Unaffecteds | | | Oldest Stringent Unaffecteds* | | |
|---|---|---|---|---|---|---|---|---|---|---|---|---|
| A2M genotype | 1/1 | 1/2 | 2/2 | 1/1 | 1/2 | 2/2 | 1/1 | 1/2 | 2/2 | 1/1 | 1/2 | 2/2 |
| APOE-ε4 dose | | | | | | | | | | | | |
| 0 | 59 | 18 | 3 | 62 | 26 | 5 | 42 | 4 | 0 | 25 | 2 | 0 |
| 1 | 100 | 39 | 3 | 89 | 37 | 2 | 33 | 12 | 2 | 22 | 7 | 1 |
| 2 | 42 | 19 | 3 | 43 | 18 | 3 | 6 | 5 | 1 | 3 | 2 | 0 |
| Total sample | 201 | 76 | 9 | 194 | 81 | 10 | 81 | 21 | 3 | 50 | 11 | 1 |
| Percent | 703 | 26.4 | 3.1 | 68.1 | 28.4 | 3.5 | 77.1 | 20.0 | 2.9 | 80.6 | 17.7 | 1.6 |

*Stringent unaffecteds are those at least as old as the latest onsetting affected subject in the family.

TABLE 2

A2M-2 Allele Frequencies Stratified on Individual APOE-ε4 Dose

| | Primary Probands | | Secondary Probands | | Oldest Unaffecteds | | Oldest Stringent Unaffecteds* | |
|---|---|---|---|---|---|---|---|---|
| | freq | $n^\$$ | freq | $n^\$$ | freq | $n^\$$ | freq | $n^\$$ |
| APOE-ε4 dose | | | | | | | | |
| 0 | .150 | 80 | .194 | 93 | .043 | 46 | .037 | 27 |
| 1 | .158 | 142 | .160 | 128 | .170 | 47 | .150 | 30 |
| 2 | .195 | 64 | .188 | 64 | .292 | 12 | .200 | 5 |
| Total | .164 | 286 | .177 | 285 | .129 | 105 | .105 | 62 |

*Stringent unaffected are those at least as old as the latest onsetting affected subject in the family.
$n^\$$ refers to the number of subjects on which the frequency is based, and is thus half the number of alleles.

2. Mantel-Haenzel Odds Ratios and Conditional Logistic Regression

Mantel-Haenzel odds ratios were calculated for the odds of being affected given the possession of at least one A2M-2 allele. These analyses were performed stratified on family using n-to-m matching, so all members of a sibship could be used and intercorrelations among siblings could be taken into account. Spielman and Ewens (Spielman, R. S., and Ewens, W. J., *Am J Hum. Genet.* 62:450–458 (1998)) have recently suggested the use of a similar analysis to test for linkage. The analyses were performed first using all unaffected siblings, and then only the stringent unaffected siblings.

Conditional logistic regression was used to control the Mantel-Haenzel odds ratio for the effect of APOE-ε4 on AD risk. Here, the outcome is disease status of each sibling, conditioning on family using an n-to-m matching paradigm, and including APOE-ε4/ε4 homozygosity as a covariate, along with a term for the interaction between APOE-ε4 and A2M-2. Like the Mantel-Haenzel odds ratio, conditional logistic regression is a standard method for analysis of data from matched sets, and can control for clustering of genotypes within families of arbitrary size. These analyses were performed using the PHREG procedure in SAS (SAS Institute, SAS Program Guide, Version 6, Cary, N.C. (1989)). These analyses were repeated using only the "stringent" unaffected siblings (those who were as least as old as the onset age of the oldest-onsetting affected sibling) in order to minimize the effect of misclassification of unaffected siblings. These analyses were also performed coding APOE-ε4 as gene dosage, and including a term for the possession of an APOE-2 allele, previously shown to decrease disease risk (Corder, E. H., et al., *Nat Genet.* 7:180–184 (1994); Farrer, L. A., et al., *JAMA* 278:1349–1356 (1997)).

The Mantel-Haenzel odds ratio (Table 3) for the risk of being affected as a function of carrying at least one A2M-2 allele was 3.56 (95% CI=$\{1.80, 7.03\}$; p 0.0003). In comparison, this same sample set yielded a similar odds ratio for the risk of being affected as a function of carrying two copies of APOE-ε4 (3.54 [95% CI=$\{1.76, 7.12\}$] p=0.0004). Thus, risk due to inheriting at least one A2M-2 allele was comparable to that conferred by APOE-ε4 homozygote status. When this analysis was restricted to stringent unaffecteds, a much smaller sample, the Mantel-Haenzel odds ratio for A2M-2 remained significant (2.27 [95% CI=$\{1. 1 9, 6.23\}$]; p=0.015). Conditional logistic regression analyses, which allow for the calculation of Mantel-Haenzel odds ratios adjusted for the effect of APOE-ε4 on AD risk are also shown in Table 3, first for all affected and unaffected siblings, and then for all affected and stringent unaffected siblings. Of note, comparable and significant magnitudes of risk were conferred by the possession of one or more A2M-2 alleles (Model 1) or by APOE-ε4 homozygosity (Model 2) and the magnitude of that risk changed little when both genes were included in the model (Model 3). There was also no evidence of an interaction between the two genes on disease risk (Model 4). The results for analyses using only the affecteds and stringent unaffecteds were similar, but less significant, as would be expected given the smaller sample size. Additional analyses were performed (not shown) coding APOE-ε4 "dose" as an ordinal variable and including A-POE-2 in the model, with no appreciable difference in the results.

TABLE 3

Conditional logistic regression for the effect of A2M and APOE-ε4 on risk for AD

| Model | Variables | est. OR | 95% CI | p-value |
|---|---|---|---|---|
| | All Affecteds and Unaffecteds | | | |
| 1 | A2M any 2 | 3.56 | (1.80, 7.03) | .0003 |
| 2 | APOE-ε4/ε4 | 3.54 | (1.76, 7.12) | .0004 |
| 3 | A2M any 2 | 3.45 | (1.71, 6.94) | .0005 |
| | APOE-ε4/ε4 | 3.45 | (1.67, 7.10) | .0008 |
| 4 | A2M any 2 | 3.40 | (1.57, 7.35) | .0018 |
| | APOE-ε4/ε4 | 3.39 | (1.51, 7.64) | .0032 |
| | interaction | 1.07 | (0.25, 4.46) | .932 |
| | All Affects and Stringent* Unaffecteds | | | |
| 1 | A2M any 2 | 2.72 | (1.19, 6.23) | .018 |
| 2 | APOE-ε4/ε4 | 3.90 | (1.62, 9.40) | .0025 |
| 3 | A2M any 2 | 2.85 | (1.21, 6.70) | .017 |
| | APOE-ε4/ε4 | 4.10 | (1.66, 10.12) | .0023 |
| 4 | A2M any 2 | 2.48 | (0.96, 6.39) | .061 |
| | APOE-ε4/ε4 | 3.61 | (1.36, 9.58) | .0099 |
| | interaction | 1.78 | (0.29, 10.9) | .533 |

*Stringent unaffecteds are those at least as old as the latest onsetting affected subject in the family.

3. Sibship Disequilibrium Test

The Sibship Disequilibrium Test (SDI) (Horvath and Laird, under revision, Am. J. Genet.) is a non-parametric sign test developed for use with sibling pedigree data that compares the average number of candidate alleles between affected and unaffected siblings. The SDT is similar to the Sib-TDT, a recently developed test that also does not require parental data (Spielman, R. S., and Ewens W. J.,Am. J Hum. Genet. (Suppl.) 53:363 (1993)), but has the advantage of being able to detect association in sibships of an arbitrary size. Like the TDT, Sib-TDT and other family-based association tests, the SDT offers the advantage of not being susceptible to errors due to admixture. Another advantage of these methods is that misclassification of affection status (e.g., due to the unaffected siblings not having passed through the age of risk) decreases the power of the test, but does not lead to invalid results. The SDT can test both linkage and linkage disequilibrium; it can only detect linkage disequilibrium in the presence of linkage, hence there is no confounding due to admixture. The null hypothesis of the SDT is that $\Theta=\frac{1}{2}$ (no linkage) or $67=0$ (no disequilibrium), i.e., $H_0$: $\delta(\Theta-\frac{1}{2})=0$. The STD program (for several platforms) and documentation may be found at ftp://sph70-57.harvard.edu/XDT/.

Because the SDT does not require parental data, and can use all information from sibships of arbitrary size, it is well-suited to the analysis of the NIMH AD data. Before using it to detect novel AD genes, the SDT was validated with the known AD gene APOE-ε4 in the sample. In an examination of 150 sibships with 286 affected and 242 unaffected individuals from the sample (n.b., the number of sibships is higher than that for the A2M analyses reported here because a greater number of families have been typed for APOE), the SDT was able to detect not only the deleterious APOE-ε4 effect but also the more difficult to detect APOE-2 protective effect (Farrer, L. A., et al., JAMA 278:1349–1356 (1997); Corder, E. H., et al., Nature Genet. 7:180–184 (1994)) not previously detected in these data (Blacker, D., et al., Neurology 48:139–147 (1997), and see Wilcox et al., in preparation).

The primary analysis of the association of A2M-2 with AD examined the probability of passing along an A2M-2 allele as a function of affection status. In order to increase the likelihood of correct classification of unaffected status, the analyses were repeated including only "stringent" unaffected siblings, those who were at least as old as the latest onsetting affected siblings, a sample of 60 families. In addition, in order to assess whether the effect differed in different APOE genotypes persisted in individuals with similar APOE genotypes, the analyses were repeated within strata defined by matching affected and unaffected siblings for APOE-ε4 gene dose. There were 18 APOE-ε4 zero-dose sibships, 21 APOE-ε4 one-dose sibships, and 11 APOE-ε4 two-dose sibships.

Analysis by the SDT revealed that A2M-2 confers significant risk for AD in the total sample (Z=4.74; p=0.00009). Once again the magnitude of the association was comparable to that observed in individuals possessing two copies of APOE-ε4 (Z=4.49; p=0.00006). The results of the SDT are shown in Table 4, including Z values (indicating the magnitude and direction of the effect), the exact p-values, the total number of sibships involved, and the number of sibships with a difference in the mean number of candidate alleles (A2M-2 or APOE-ε4) between affected and unaffected siblings (i.e., the effective sample size). This effect persisted when only the stringent unaffected siblings were used, and within the subset of sibships concordant for zero or one "dose" of APOE-ε4 (data not shown). To provide further validation of the SDT, the Sibling TDT (Spielman, R. S. and Ewens, W. J.,Am. J. Hunt Genet. 62:450–458 (1998)) (Sib-TDT) was applied. The Sib-TDT also revealed significant association between A2M and AD (Z=3.61, p=0.0002).

TABLE 4

Sibling disequilibrium test* results for association between the A2M-2 allele and AD

| Sample | Number of sibships | Effective sample size[#] | Z[$] | p |
|---|---|---|---|---|
| A2M-2: Total sample | 104 | 40 | 4.74 | 0.00009 |
| A2M-2: Sibships including a stringent unaffected[@] | 60 | 27 | 3.47 | 0.0059 |
| APOE-ε4: Total sample | 104 | 47 | 4.49 | 0.00006 |

*Horvath and Laird, under revision, AJHG.
[#]The effective sample size is the number of sibships with a difference in the mean number of candidate alleles (A2M-2, APOE-ε4) between affected and unaffected siblings.
Z[$] values indicate the magnitude and direction of the effect.
[@]Stringent unaffecteds are those at least as old as their oldest onsetting affected sibling.

4. Age of Onset Based Techniques

In order to see if A2M effects appeared to operate via changes in age of onset, affected individuals were examined according to A2M genotype, stratifying on or controlling for the powerful effect of APOE-ε4. First, this was examined graphically using Kaplan Meier curves (data not shown) including all affected and unaffected individuals, first stratifying on A2M genotype alone, and then on A2M-2 carrier status and APOE-ε4 dose. Second, the mean ages of onset of primary and secondary probands were compared by A2M genotype overall, and stratified on APOE-ε4 gene dose. Third, analysis of variance (performed separately for primary and secondary probands) was used, including first only A2M genotype (defined as any 2 vs. none), then only APOE genotype (defined as APOE-ε4 gene dose or APOE-ε4/ε4 vs. not), then both, and then both plus an interaction term.

Although A2M-2 appeared to increase risk for AD, unlike APOE-ε4, it did not appear to decrease age of onset of AD. This is shown graphically in Kaplan Meier curves of the sample as a whole, stratified first on A2M genotype alone and then on both the presence of an A2M-2 allele and APOE-ε4 dose. These graphs clearly show that inheritance of the APOE-ε4/ε4 genotype lowers age of onset, irrespective of A2M genotype. However, no difference in age of onset was conferred by A2M genotype for the overall sample or within any APOE-ε4 dose stratum.

The mean ages of onset for primary and secondary probands for each A2M genotype overall, and stratified according to individual APOE-ε4 dose showed no effect of A2M genotype on age of onset of AD (Table 5), but did show the expected decline in age of onset homozygous for APOE-ε4. Analysis of variance of primary (and secondary, performed separately) probands showed no effect of A2M genotype on age of onset, but did show a significant effect of the APOE-ε4/ε4 genotype on age of onset.

TABLE 5

Age of onset of AD by A2M genotype, stratified on individual APOE-ε4 dose

| APOE dose | A2M Genotype | Primary Probands | | | Secondary Probands | | |
|---|---|---|---|---|---|---|---|
| | | 1/1 | 1/2 | 2/2 | 1/1 | 1/2 | 2/2 |
| 0 | n | 59 | 18 | 3 | 62 | 26 | 5 |
| | m (sd) | 73.0 | 76.2 | 76.3 | 74.7 | 75.7 | 76.4 |
| | | (8.7) | (10.0) | (3.5) | (8.2) | (8.2) | (7.2) |
| 1 | n | 100 | 39 | 3 | 89 | 37 | 2 |
| | m (sd) | 71.7 | 73.0 | 73.0 | 73.8 | 73.0 | 70.0 |
| | | (7.4) | (7.9) | (7.9) | (5.9) | (6.0) | (4.2) |
| 2 | n | 42 | 19 | 3 | 43 | 18 | 3 |
| | m (sd) | 68.4 | 62.8 | 67.0 | 65.6 | 67.9 | 65.0 |
| | | (6.9) | (6.0) | (4.4) | (6.7) | (8.8) | (7.9) |
| Total | n | 201 | 76 | 9 | 194 | 81 | 10 |
| | m (sd) | 71.4 | 71.7 | 72.1 | 72.3 | 72.7 | 71.7 |
| | | (7.8) | (9.5) | (6.4) | (7.3) | (7.8) | (8.2) |

5. Traditional Linkage Analysis and Related Techniques

In order to determine if there was evidence for linkage in the A2M region, and in particular whether A2M might be related to the recent reports of linkage to the centromeric region of chromosome 12 (Pericak-Vance, M. A., et al., JAMA 278(15):1237–1241 (1997)), a variety of genetic linkage analytic techniques were performed. For these analyses, all families were divided into "tiers" according to the criteria of Pericak-Vance et al. (Pericak-Vance, M. A., et al., JAMA 278(15):1237–1241 (1997)): Tier 1 (30 families) is comprised of families in which all affecteds were APOE-ε4/ε4; Tier 2 (131 families) is comprised of families not in Tier 1 in which all affecteds were APOE-ε4 carriers; and Tier 3 (126 families) is comprised of families in which at least one affected did not carry an APOE-ε4 allele. It should be noted that Pericak-Vance et al. found evidence for linkage to chromosome 12 markers only for Tier 3. All analyses were run on the entire sample and on each of these three tiers. In addition, because the analyses in Pericak-Vance et al. were confined to families with all onsets at 60 or above, and in which AD was evident in at least two generations, the analyses were repeated using the 259 families meeting these criteria (24 in Tier 1, 118 in Tier 2, and 117 in Tier 3).

The first technique used was conventional linkage analysis using two autosomal dominant disease models. The first model was an affecteds only analysis based on the model used by Pericak-Vance et al. (Pericak-Vance, M. A., et al., JAMA 278(15):1237–1241 (1997)): a gene frequency of 0.001 and a phenocopy rate of 0.05. The other main model was an age-curve model assuming a normal distribution of disease onset with a mean of 71.4 and sd of 8.7 (n.b., these are the observed values in the Genetics Initiative sample, and are very similar to those used in Pericak-Vance et al. (Pericak-Vance, M. A., et al., JAMA 278(15):1237–1241 (1997)), a disease gene frequency of 0.01, and a fixed phenocopy rate of 0.10 (n.b., this value was used for the Probable AD cases [70.3 % of the subjects] and for the computation of partial penetrances for unaffected subjects; a penetrance of 0.05 was used for the Definite AD cases [22.2% of the subjects], and 0.14 for the Possible AD cases [7.5% of the subjects]). However, because these analyses were done in part in an attempt to replicate the findings of Pericak-Vance et al., additional models (all using the normal onset distribution described above) considered consistent with AD genetics and prevalence were also tested, including the inventors' best approximation of the age curve model used by Pericak-Vance et al. (Pericak-Vance, M. A., et al., JAMA 278(15):1237–1241 (1997)), with a disease gene frequency (q) of 0.001 and a phenocopy rate ($\phi$) of 0.05; q=0.01 and $\phi$ 0.05; q=0.02 and $\phi$=0.05; q=0.02 and $\phi$0.10. All lod score analyses were performed in Fastlink (Terwilliger, J. D., Ott, J., Handbook of Human Genetic Linkage. Baltimore: Johns Hopkins UP, (1994)).

The second technique was multipoint non-parametric linkage analysis (FIG. 2) using the program GENE-HUNTER (Kruglyak, L., et al., Am J Hum Genet 58:1347–1363 (1996)(software available from Kruglyak et al. by anonymous ftp at ftp-genome.wi.mit.edu or from their World Wide Web site http://www-genome.wi.mit.edu/ftp/distribution/software/genehunter)), a multipoint non-parametric linkage program accommodating full pedigrees, and reporting non-parametric lod (NPL) scores.

The last technique was the multivariate sibship analysis package ASPEX (Affected Sibpair Exclusion Mapping; ftp://Iahmed.stanford.edu/pub/aspex/), which is based on allele sharing within sibships. The analyses were performed using the Sib-Phase program, using fixed, allele frequencies based on those observed in the data (see below) to estimate IBD probabilities when parental information is missing, and using no dominance variance. In addition, exclusion analysis was performed setting the ASPEX parameter "risk" (which is roughly equivalent to X, the recurrence risk in relatives) at 2, a reasonable value for AD based on family data (Farrer, L. A., et al., Neurology. 40(3 Pt 1) 395–403 (1990)).

For all types of analysis, allele frequencies were computed from the data, but rare alleles were adjusted up to a frequency of 0.01 (with a compensatory small decrease in the frequency of the most common alleles) in order to minimize the possibility of a false positive result. All analyses were repeated using the uncorrected frequencies.

For the multipoint techniques (ASPEX and GENEHUNTER), maps of the region were constructed based on Krauter et al., 1995 (Krauter, K., et al., Nature 377:321–333 (1995)). The map used is shown in FIG. 1, which indicates the markers used in the present study and those reported in Pericak-Vance et al. (Pericak-Vance, M. A., et al., JAMA 278(15):1237–1241 (1997)).

In the interest of clarity and simplicity, nominal p-values are reported here. Most of the methods used involve multiple comparisons (e.g., testing across multiple genetic models, or using multiple different approaches to the same question). Therefore, only p-values of 0.01 or less should be viewed as significant (Pocock, S., et al., N. Engl. J. Med 317:426–432 (1987)).

Genetic linkage analysis in the sample of 286 families was performed next for A2M and a set of chromosome 12 markers (FIG. 1) including several centromeric markers recently reported to be linked to AD by Pericak-Vance et al. (Pericak-Vance, M. A., et al., JAMA 278(15):1237–1241 (1997)). A2M resides roughly 27 cM of the centromeric marker, D12S1042, which yielded the highest maximum 2-point lod-score (2.7) by affecteds-only analysis in the Pericak-Vance et al. study ((Pericak-Vance, M. A., et al., *JAMA* 278(15):1237–1241 (1997); Krauter, K., et al., *Nature* 377:321–333 (1995)). Besides setting out to determine whether the association between A2M-2 and AD could be detected by traditional linkage analyses and could be explained by the previous linkage findings of Pericak-Vance et al. (Pericak-Vance, M. A., et al., *JAMA* 278(15):1237–1241 (1997)), the inventors also attempted to confirm the previous linkage findings in the sample set.

Initially affecteds-only lod score analyses were performed, which showed that lod scores for A2M and virtually all markers were less than 0 out to a recombination fraction of 30 cM. Lod scores from affecteds only analyses were also strongly negative in Tier 3 (in which at least one affected in each family does not carry the APOE-$\epsilon$4 allele). Tier 3 is analogous to the subgroup of AD families for which Pericak-Vance et al. (Pericak-Vance, M. A., et al., *JAMA* 278(15):1237–1241 (1997)) reported evidence for linkage to AD. The lod scores were similarly negative in Tier 2 (families in which all affecteds are APOE-$\epsilon$4 carriers, but at least one is a non-homozygote). However, in Tier 1 (families in which all affecteds are APOE-$\epsilon$4/$\epsilon$4), there was a weak but non-significant signal: maximum lod score of 1.23 at $\Theta$=7 cM for D12s1042 and 0.74 at $\Theta$=12 cM for D12s1090, 7cM distal. The results of several different age curve models (not shown), including that used by Pericak-Vance et al. (Pericak-Vance, M. A., et al., JAMA 278(15):1237–1241 (1997)), were also strongly negative, except in Tier 1, where the results were slightly positive yet nonsignificant as in the affecteds-only analyses.

Next, multipoint analyses were performed using GENE-HUNTER (Kruglyak, L., et al., *Am J Hum Genet* 58:1347–1363 (1996)(software available from Kruglyak et al. by anonymous ftp at ftp-genome.wi.mit.edu or from their World Wide Web site http://www-genome.wi.mit.edu/ftd/distribution/software/genehunter)) (FIG. 2) and the results were similarly negative. NPL scores for A2M and virtually all markers were less than 0 for the sample as a whole (FIG. 2A) and for Tiers 2 (FIG. 2C) and 3 (FIG. 2D) (analogous to the subgroup analyzed by Pericak-Vance et al. (Pericak-Vance, M. A., et al., *JAMA* 278(15):1237–1241 (1997)). However, in Tier 1 (FIG. 2B), in which all affecteds are APOE-$\epsilon$4/$\epsilon$4, there was again a weak but non-significant signal: NPL=1.37 at D12s1042 p=0.08) and 1.21 at D12s1090 (p=A1).

Multipoint sibpair analyses in the program ASPEX were similarly negative with maximum lods of 1.31 for D12s1042, and .91 for D12s1090. Of note, exclusion analyses with "risk" (corresponding approximately to $\lambda$, the recurrence risk in relatives) set at 2 performed in ASPEX yielded extremely negative lod scores throughout the region for the sample as a whole (lod<–8), and for Tiers 2 and 3 (lod<–3). For Tier 1, consistent with the non-significant peak observed in several analyses, the region provided no significant results for genetic linkage, but could not be entirely excluded.

Next, all of the above analyses were repeated using uncorrected allele frequencies. The analyses defining the sample was also repeated as in Pericak-Vance et al. (Pericak-Vance, M. A., et al., *JAMA* 278(15):1237–1241 (1997)), i.e., using only the 259 families in which all sampled affected individuals experienced onset of AD at 60 or above, and in which at least 3 cases of AD spanning 2 generations were evident. The results of all of these analyses were similar to those described above, and did not confirm the findings presented in Pericak-Vance et al. (Pericak-Vance, M. A., et al., *JAMA* 278(15):1237–1241 (1997)). Thus, similarly negative findings were obtained using multiple genetic models, multiple family selection criteria, and multiple statistical methods. In all cases, the inventors were unable to confirm the previous finding of linkage of AD to the centromeric region of chromosome 12 reported by Pericak-Vance et al. (Pericak-Vance, M. A., et al., *JAMA* 278(15):1237–1241 (1997)). It should also be noted that traditional linkage and multipoint analyses were not able to detect genetic linkage between A2M and AD. This is most likely due to the lack of informativeness of the biallelic A2M polymorphism in a sample of this nature. However, evidence was found for linkage of chromosome 12 to AD using other markers, including D12598 and DRS358, (Wu, W. S., et al., *JAMA* (in press, 1998)) that were located much closer to A2M than the markers used in the genetic analysis described above.

C. Discussion

These analyses provide evidence of a link between A2M and risk for Alzheimer's disease, and demonstrate that inheritance of the A2M-2 allele, confers three-to four-fold increased risk for AD and is strongly associated with AD in the SDT. Moreover, in these analyses, the inheritance of one or two A2M-2 alleles; conferred a degree of risk for AD comparable to that associated with inheriting two APOE-$\epsilon$4 alleles. The association of A2M-2 and AD was not accounted for by differences in the dose of the APOE-$\epsilon$4 allele, and did not vary when the APOE-$\epsilon$4 effect was controlled for in a multivariate setting.

Although, A2M maps within 30 cM of the chromosome 12 markers reported to be linked to AD (Pericak-Vance, M. A., et al., *JAMA* 278(15):1237–1241 (1997); Krauter K., et al., *Nature* 377:321–333 (1995)), the observed genetic association between A2M and AD described here does not appear to account for these linkage findings. Moreover, the inventors were unable to confirm the linkage reported by Pericak-Vance et al. (Pericak-Vance, M. A., et al., *JAMA* 278(15):1237–1241 (1997)) in the present data set despite rigorous attempts to duplicate that study. The inventors were also unable, using traditional genetic linkage and multipoint analyses, to demonstrate genetic linkage of A2M to AD, which may reflect the limited power of such analyses in a data set of this nature, especially in comparison to family-based association methods in the analysis of a candidate gene.

Although these data suggest that A2M-2's association with AD may be as strong as that of APOE-$\epsilon$4, A2M-2 does not appear to share APOE-$\epsilon$4's effect on age of onset of AD (based on the similarity in age of onset among affecteds with different A2M genotypes seen graphically and analytically). Thus, rather than conferring risk by modifying the age of onset, as appears to be the case with APOE-$\epsilon$4, it appears that A2M-2 confers risk for developing the disease at any age. The mode of inheritance for the observed effect of A2M-2 on AD could not be assessed in the present study. For example, it is unclear whether A2M acts alone or in conjunction with other genes to confer increased risk for AD. In addition, due to the small number of A2M-2 homozygotes, the inventors were unable to assess for a difference in effect of one versus two doses of A2M-2 on risk for AD.

Since increased APOE-$\epsilon$4 dose correlated with an earlier age of onset among AD patients with the A2M-2 allele, it is possible that APOE-$\epsilon$4 influences the age of onset in individuals who are a priori more susceptible to developing AD due to the inheritance of A2M-2. A2M-2 may represent a relatively prevalent public polymorphism (25–30%) that confers susceptibility for AD, with age of onset of the disease in susceptible individuals modified by APOE-ε4 dosage. Further investigation will be necessary to identify other genes that may epistatically interact with A2M and/or APOE to determine either risk and/or the age of onset of AD. The genetic model suggested by these current findings is in agreement with the recent observations of Meyer et al. (Submitted), in a study of nearly 5,000 elderly individuals, that APOE genotype influences "when" but not "whether" AD will develop in a priori susceptible individuals, and that regardless of APOE genotype, roughly 50% of the population will not develop AD by age 100. In view of these findings, inheritance of mutations in genes like A2M or other genes yet to be identified may be necessary to confer initial predisposition for the occurrence of AD, while genes like APOE modify age of onset in susceptible individuals.

This heuristic genetic model for AD lends itself to an intriguing biological model for AD neuropathogenesis in view of the known physiological roles of $\alpha_2M$, apoE, APP, and their common receptor, LRP. $\alpha_2M$ is a pan-protease inhibitor which is constitutively expressed in brain and upregulated together with LRP during acute phase brain injury (e.g., by ischemia, stroke). $\alpha_2M$ has been shown to bind a wide range of proteases, growth factors, cytokines, and small polypeptides, and has been detected in pyramidal neurons and neuritic plaques in affected regions of AD brain (Borth, W., FASEB 6: 3345–3353 (1992); Bauer J., et al., FEBS 285:111–114 (1991)). Recently, $\alpha_2M$ was shown to tightly bind AP and mediate its clearance via endocytosis through LRP (Narita, M., et al., *J Neurochem.* 69:1904–1911 (1997)), and, in complex with a serine protease, has been shown to degrade Aβ (Qiu, W. Q., et al., *J. Biol Chem.* 271:8443–8451 (1996)). Thus, $\alpha_2M$ may clear and/or degrade secreted Aβ from the brain parenchyma, thereby governing the rate of Aβ fibrillogenesis and β-amyloid deposition. Indeed, $\alpha_2M$ has also been shown to attenuate both Aβ fibril formation and neurotoxicity in vitro (Du, Y., et al., *J. Neurochem.* 69:299–305 (1997); Hughes, S. R., et al., *Proc. Natl. Acad Sci.* (USA) 95:3275–3280 (1998); Du, Y., et al., *J. Neurochem.* 70:1182–1188 (1998)). Since apoE, like $\alpha_2M$, can bind Aβ and utilizes LRP as its major neuronal receptor in brain, these two proteins could conceivably compete for binding to LRP and Aβ. Thus, the clearance and degradation of Aβ in the brain parenchyma could potentially be impaired by increased amounts of apoE (Zhang, Z., et al., *Int. J Exp. Clin. Invest.* 3:156–161 (1996)), or the presence of apoE isoforms that have higher affinity for LRP or Aβ.

Interestingly, APOE promoter polymorphisms, which upregulate transcription of APOE, have recently been shown to be associated with AD and to be in linkage disequilibrium with APOE-ε4 (Bullido, M. J., et al., *Nature Genet.* 18:69–71 (1998); Lambert, J. C., et al., *Hum. Mol. Genet.* 7:533–540 (1998)). Additionally, allelic distortion resulting in higher levels of message for APOE-ε4 (relative to APOE-3) has been reported to occur in the brains of AD patients but not age-matched controls (Lambert, J., et al., *Hum. Mol. Genet.* 6:2151–2154 (1997)). The absence of apoE in transgenic mice expressing an FAD mutant form of APP has been shown to attenuate β-amyloid deposition (Bales, K. R., et al., *Nat. Genet.* 17:263–264(1997)). Given these findings, it is possible that increased levels of APOE expression may modify age of onset of Aβ perhaps by interfering with $\alpha_2M$-mediated clearance and degradation of AD via LRP-mediated endocytosis and direct degradation by α2M-protease complexes, respectively, resulting in greater amyloid burden. The inventors have recently localized LRP to synaptic terminals where impaired clearance of $\alpha_2M$ complexes (e.g., containing Aβ) could conceivably promote synaptic degradation, a major neuropathological feature of AD (Kim et al., Submitted). A heuristic genetic model in which A2M-2 confers susceptibility to AD while APOE genotype modifies the age of onset readily lends itself to this biological model. In further support for this model, an exon 3 polymorphism in LRP has also recently been shown and confirmed to be genetically associated with AD (Kang, D. E., et al., *Neurology* 49:56–61 (1997); Lendon, C. L., et al., *Neurosci. Lett.* 222:187–190 (1997); Wavrant-DeVrieze, F., et al., *Neurosci. Lett.* 227:68–70 (1997); Hollenbach, E., et al., *Neurology,* In Press (1998)). However, another polymorphism consisting of a trinucleotide repeat in the 5' untranslated region of LRP was excluded from being genetically linked or associated with AD (Lendon, C. L., et al., *Neurosci. Lett.* 222:187–190 (1997); Clatworthy, A. E., et al.,*Arch. Neurol.* 54:1289–1292 (1997); and Scott, W. K., et al., *Neurogenetics* 1: 179–183 (1998)).

The data above indicate that A2M is a novel AD gene that predisposes, in particular, carriers of the A2M-2 deletion to increased risk for AD, but without modifing age-of-onset. A2M, together with the gene for its receptor, LRP, and the genes encoding two other LRP ligands, APOE, and APP, have now all been genetically linked to AD. Thus it is plausible that all four of these proteins participate in a common pathogenic pathway leading to AD-related neurodegeneration.

The A2M-2 exon splice site deletion occurs at the 5' splice acceptor for exon 18. One would predict that this deletion would cause the skipping or deletion of exon 18, which encodes the second half of the bait domain of α2M. The bait domain is required for α2M to bind and trap a wide range of proteases. The inventors postulate that the loss of a fully functional bait domain in a portion of α2M molecules would result in the promotion of AD-related neuropathogenesis in a variety of different ways. One possibility is that the loss of the bait domain results in decreased ability to degrade and clear Aβ from the brain (e.g., in synapses). However, the possible consequences of the loss of a filly functional bait domain are actually immense in scope given the incredibly wide range of proteases that α2M can bind, and the multifold downstream events which may occur as a result of the attenuation of global protease regulation (e.g., following injury to the brain due to stroke or head trauma). The location of the A2M-2 exon splice site deletion suggests that the protease inhibitory function of $\alpha_2M$ may protect against AD. Thus, the possibility that any of the multifold functions of α2M may be adversely affected by A2M-2 cannot be ruled out. For example, in addition to binding to LRP, α2M can also bind to the α2M signalling receptor (α2MSR), which is involved in cell signalling events (e.g., activation of phosphatidylinositol 3-kinase) modulating intracellular calcium levels (Misra, U. K. and Pizzo, V., *J Biol. Chem.* 273:13399–13402 (1998)).

Example 2

The G Allele

A. Genotype and Allele Frequencies

An initial exploratory experiment was used to test for the possibility that the less common "G" allele of A2M would be associated with Alzheimer's disease. Because of the potential for error due to multiple hypothesis testing, an initial data set was used as an exploratory data set, with the intent of formulating specific hypotheses that would then be tested formally with a second independent data set.

In the initial data set, 90 non-Alzheimer's individuals, age-compatible, who had either undergone screening tests with the Blessed dementia scale (Blessed, G., et al., Br. J. Psychiatry 114:797–811 (1968)) or whose DNA had been isolated from autopsy material and were demonstrated to not have Alzheimer's disease, and 171 individuals who either had a clinical diagnosis of Alzheimer's disease or neuropathologically proven Alzheimer's disease were genotyped (Table 6). The 90 control subjects were primarily spouses of the AD subjects.

Figure 3:
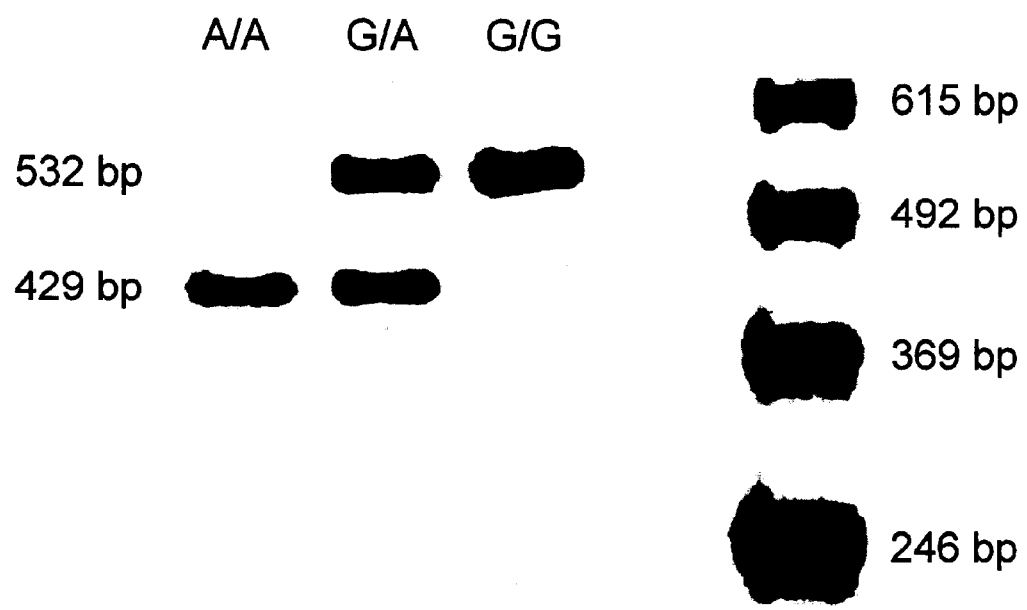
FIG. 3 Alpha-2-Macroglobulin Val$^{1000}$ Polymorphism Genotyping.

Genotypes were determined by polymerase chain reaction amplification of DNA and RFLP analysis using MboI (FIG. 3). Genomic DNA isolated from brain tissue and blood was amplified by polymerase chain reaction (PCR) in the presence of oligonucleotide sense primer C23 (SEQ ID NO: 3) and antisense primer AS24 (SEQ ID NO: 4), 10 mM Tris-HC1, 50 mM KC1 (pH 8.3), 1.5 mM MgCl$_2$, 5 mM dNTPs, 5 pmol each primer, and 1.25 U Taq DNA polymerase. The PCR was carried out in a touchdown procedure that stepped down the annealing temperature to increase primer specificity as follows: 1 cycle at 94° C.-5 min; 4 cycles at 94° C.-30 sec, 65° C.-30 sec, 72° C.-1 min; 4 cycles at 94° C.-30 sec, 62° C.-30 sec, 72° C.-1 min; 4 cycles at 94° C.-30 sec, 59° C.-30 sec, 72° C.-1 min; 20 cycles at 94° C.-30 sec, 56° C.-30 sec, 72° C.-1 min; and 1 cycle at 72° C.-5 min. For each reaction mixture, 10 units of MboI were added to the amplified product of 615 bps and digestion carried out at 37° C. for 3 hours, producing fragments of 532 and 429 bps. The digested product was loaded onto a 2% agarose gel treated with ethidium bromide (0.005%) and electrophoresed for 2 hours under constant voltage (150V), which is sufficient to separate the digested product so that the 532 and 429 bp bands can be distinguished. After electrophoresis, DNA fragments were visualized by UV illumination using a Biorad Geldoc system. Incomplete digestion was monitored by looking for the presence of the 615 bp fragment.

For the statistical analyses below, comparisons of A2M allele frequency (proportion of chromosomes in which an allele is present) and genotype frequency (proportion of individuals with a genotype) were performed with 2×2 tables using Fisher's exact test for significance. Age of onset of Alzheimer's disease was normally distributed and compared by t-test. Multivariate analysis for odds of AD was performed by logistic regression with APOE genotype coded according to the presence or absence of APOE-ε4. Similar results were obtained when the group with APOE-ε4 was coded separately as heterozygotes or homozygotes for this allele. Odds ratios are presented with 95% confidence intervals (CI). All analyses were performed with Stata software (Stata Corporation, College Park, Tex.). All significance tests were two-tailed.

The results of the genotype and allele frequency analysis for the exploratory data set suggested that the A2M Val, Ile$^{2000}$ polymorphism may be a genetic risk factor for Alzheimer's disease, and warranted further investigation. In the control series the G allele frequency was 0.28 and 6 of 90 individuals contained the A2M G/G genotype (0.067). In the Alzheimer's disease set, the G allele frequency was 0.32. The A2M G/G genotype frequency was increased in the Alzheimer's group at 0.12 (Table 6).

TABLE 6

Overrepresentation of the A2M G/G genotype in AD

|  | N | G allele (%) | G/G genotype (%) |
|---|---|---|---|
| Exploratory Data Set |  |  |  |
| Control | 90 | 0.28 | 0.07 |
| AD | 171 | 0.32 | 0.12 |
| Hypothesis Testing Data set |  |  |  |
| Control | 359 | 0.32 | 0.07 |
| AD | 566 | 0.34 | 0.12* |
| Combined Data Set (Total) |  |  |  |
| Control | 449 | 0.32 | 0.07 |
| AD | 737 | 0.34 | 0.12** |

*p < 0.05
**p < 0.01

To formally test the hypothesis that the A2M G/G genotype of A2M is overrepresented in Alzheimer's disease, another data set was collected and genotyped from additional independent groups of patients and controls. Power analysis showed that more than 500 AD and control individuals would be necessary to have an 80% chance of showing a difference between genotype frequencies of 0.07 and 0.12. Therefore, AD patients and control individuals collected from several sites were used to form a sample of this size. This second data set consisted of individuals who met the criteria for AD or control individuals used for the initial data set, and included 387 sporadic AD and 359 control individuals collected from the Massachusetts General Hospital Memory Disorder Unit and from a consortium of European Centers (University of Hamburg, Germany; University of Basel, Switzerland; University of Brescia, Italy) and 179 probands from NIMH Genetics Initiative sample (Blacker, D., et al., Neurology 48:139–47 (1997)).

The results from the second data set supported the hypothesis, with G/G genotype 0.07 in controls and 0.12 in AD (p=0.05, Fisher's exact test) (Table 6). The G allele was not over-represented in AD in this data set (control=0.32, AD=0.34) (Table 6). No difference in age of onset between G/G and non G/G was found in the second data set. Multivariate analysis showed that site of collection did not influence genotype frequencies. In addition, when the rate in controls was compared to the subset of 387 clinic based AD cases (G/G frequency=11.4%, p=0.06) and the subset of 179 familial AD samples (G/G frequency=12.7%, p=0.056), essentially equal overrepresentation of G/G was found in each. These data support an association of the G/G genotype with AD.

Next, a series of exploratory analyses were done using pooled data from both data sets (737 AD patients and 449 controls). The G/G genotype was present in 11.9% of the Alzheimer patients, and 7.3% of the controls (p<0.01, Fisher's exact test). The genotype frequency in controls was consistent with Hardy Weinberg equilibrium. Age of onset was not different between AD patients with G/G (70.0±9.2, X±SD) and non-G/G carriers (70.6±9.1).

B. Multivariate Model Controlling for Presence of APOE-ε4 and Gender

A multivariate logistic model that controlled for the presence of the APOE-ε4 allele and gender showed an odds ratio of 1.88 (95% CI 1.20–2.95; p<0.01) for the presence of A2M G/G genotype. The presence of APOE-ε4 in this model was associated with an odds ratio of 4.21 (95% CI 3.20–5.55; p<0.001). The odds ratio for the combination of A2M G/G and APOE-ε4 is 9.68 (95% CI 3.91–24.0; p<0.001) relative to those with neither risk factor.

To explore whether the A2M G/G mediated risk was influenced by the presence or absence of APOE-ε4, the sample was stratified by the presence or absence of APOE-ε4. Similar overrepresentations of the A2M G/G genotype were seen in the strata with or without APOE-ε4, suggesting that the effects of the two risk factors are independent. Multivariate analysis for interaction between the A2M GIG genotype and either APOE-ε4 or gender demonstrated no interactions (p>0.5 for interaction terms). Analysis based on the Mantel-Haenzel estimator suggested no heterogeneity of odds ratios between strata with and without APOE-ε4 (p>0.5), consistent with the absence of an interaction between A2M and APOE-ε4 in our logisteic regression model.

C. Biological and Neuropathological Effects of G/G Genotype

Also investigated were the possible biological effects of inheritance of the A2M G/G genotype. Previous studies of A2M immunohistochemistry performed on Alzheimer's brain suggested that senile plaques in different patients stained with varying intensity (Rebeck, G. W., et al, *Ann. Neurol.* 37:211–217 (1995)). The possibility that this variability was due to different genotypes was investigated by immunostaining samples from 8 AD cases known to be G/G or A/A genotype.

Sections of brain tissue from AD patients were incubated with anti-$\alpha_2$M antibody (1:500) from Zymed. A goat Cy-3 linked secondary antibody (Jackson Immunoresearch) was used to visualize immunostaining. In some instances, double immunofluorescence was carried out with an Aβ counterstain (antibody 10D5, obtained from Dr. D. Schenk, Athena Neurosciences) using bodipyfluorescein linked secondary antibody (Molecular Probes) as the second fluorochrome. In all instances, $\alpha_2$M immunoreactivity was present robustly on senile plaques, astrocytes, and neurons, and no qualitative differences were observed between the genotype groups.

Next explored was the effect inheritance of the A2M G/G genotype on the neuropathological phenotype of Alzheimer's disease. In an earlier study, reported in Gomez-Isla et al. (Gomez-Isla, T., et al., *Ann. Neurol.* 41:17–24 (1997)), stereological techniques and quantitative image analysis were used to measure the amount of amyloid burden present in neocortical association area surrounding the superior temporal sulcus (STS) and the number of neurofibrillary tangles present in the same region in normal and Alzheimer brain. Thirty-one (31) of the previously analyzed AD cases (Gomez-Isla, T., et al., *Ann. Neurol.* 41:17–24 (1997)) were genotyped and selected for further analysis. Initial inspection of the data suggested an increase in Aβ in individuals who were A/G or G/G, with no difference between these two groups. A statistically significant increase in Aβ deposition was seen comparing the G containing cases to the non-G containing cases (8.8±2.8% vs 6.6±1.9%, p<0.03, unpaired t test) (Table 7). The effect appears to be primarily due to the presence of at least one G allele, in that no difference between A/G and G/G genotypes was observed although the sample size limits the power of this comparison. There were no statistically significant differences in neurofibrillary tangle number with G alleles, suggesting a specific effect on Aβ deposition.

TABLE 7

Neuropathological Correlates of A2M Genotype

| Genotype | n | Amyloid burden (%) | Neurofibrillary Tangles (× $10^3$) |
|---|---|---|---|
| A/A | 10 | 6.6 ± 1.9* | 6.9 ± 4.1 |
| A/G + G/G | 21 | 8.8 ± 2.8** | 9.0 ± 5.0*** |

*mean ± SD
**p < 0.03 t test
***n = 17 for this measurement

D. Discussion

These analyses provide further support for an association between A2M, and in particular the A2M G/G genotype, and AD. In order to overcome some of the difficulties inherent in exploratory studies of genetic risk factors, independent data sets were used to first generate, then test the hypothesis that the G/G genotype is associated with Alzheimer's disease. Exploratory studies of genetic risk factors run the risk of Type I errors because of the large number of hypotheses that are either explicitly or implicitly being tested. Alternatively, type II errors can occur if sample size is insufficient. The two separate control populations, used to overcome these difficulties, gave identical genotype frequencies. Moreover, the hypothesis testing data set was itself made up of two groups (sporadic AD and probands from a multicenter study of Alzheimer's disease sib pairs and small families) each of which gave essentially identical genotype frequencies and overrepresentation of the G/G genotype. The A2M G/G effect was not dependent on APOE genotype, and the effect was additive and substantial—the odds ratio of G/G in the presence of an APOE-ε4 allele showed an almost 10 fold increased risk. Power analysis using the size of effect observed in our combined data set (using about 500 samples) suggests that a group size of 578 controls and 578 Alzheimer's disease patients would be necessary to have an α of 0.05 and a β of 80% for the hypothesis that the G/G genotype is increased from 0.07 to 0.12 in Alzheimer's disease.

The association of the A2M G/G genotype as a risk factor in Alzheimer's disease leads to several interesting mechanistic interpretations. Previous studies have shown that $\alpha_2$M immunostains SP and have implicated $\alpha_2$M in amyloid precursor protein metabolism (Ganter, U., et al., *FEBS* 282:127–131 (1991)) as well as possible interactions with binding Aβ (Du, Y., et al., *J Neurochem.* 69:299–305 (1997)) and mediating degradation of Aβ (Qiu, W. Q., *J Biol Chem.* 271:8443–8451 (1996); Zhang, Z., et al., *Int. J Exp. Clin. Invest.* 3:156–161 (1996)). $\alpha_2$M-Aβ complexes undergo endocytosis via $\alpha_2$M-r/LRP (Narita, M., et al, *J Neurochem.* 69:1904–1911 (1997)). $\alpha_2$M associates with Aβ and prevents fibril formation (Hughes, S., et al., *Proc. Natl. Acad Sci.* 95:3275–3280 (1998)). In addition, $\alpha_2$M can be viewed as a (sub) acute phase reactive molecule and as a potent protease inhibitor which might participate in the inflammatory response in Alzheimer brain. Interestingly, $\alpha_2$M has also been implicated as a trophic factor, possibly as a result of binding and transporting a number of polypeptide growth factors and cytokines (Borth, W., *FASEB* 6:3345–3353 (1992)). Like Apo E, $\alpha_2$M may serve as a binding protein for targeting various bioactive molecules to their site of action or clearing them (Rebeck, G. W., et al., *Ann. Neurol.* 37:211–7 (1995)). Moreover, the fact that apoE and APP, two other LRP ligands are clearly involved in the pathophysiology of Alzheimer's disease, supports the hypothesis that a link exists between A2M and risk for Alzheimer's disease. In fact, a polymorphism in LRP has recently been reported in two studies showing a genetic association with Alzheimer's disease (Kang, D. E., et al., *Neurology* 49:56–61 (1997); Hollenbach, E., et al, *Neurology* 50:1905–7 (1998)).

The likelihood that A2M is a risk factor is also supported by the association between the A2M-2 allele and AD discussed in Example 2 above. The combined analyses of the A2M-2 and the A2M-G alleles indicate that these two mutations act independently of each other to confer an increased risk of AD, i.e., inheritance of A2M-2 is not genetically linked to inheritance of A2M-G in the same AD patients. This is based on the observation that the A2M-G allele frequently segregates with the A2M-1 allele. In 160 random individuals, 56 of 58 obligate A2M-G chromosomes were found to carry the A2M-1 allele (13 out of 14 obligate A2M-2 chromosomes carry the A2M-A allele).

In summary, A2M appears to be a novel AD gene that predisposes, in particular, individuals with either the A2M-2 or the A2M G/G genotype to increased risk for AD, but without modifying age-of-onset.

Modifications of the above-described modes for carrying out the invention that are obvious to persons of skill in medicine, genetics, molecular biology, biochemistry and/or related fields are intended to be within the scope of the following claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

Although the foregoing invention has been described in some detail by way of illustration and example for purposes of clarity of understanding, it will be obvious that certain changes and modifications can be practiced within the scope of the appended claims.

What is claimed is:

1. A method of assessing an individual's risk of developing AD comprising genotyping the A2M locus of an individual to determine whether said individual possesses an A2M-2 allele, and drawing a conclusion regarding said individual's risk of developing Alzheimer's disease based on the possession of one or more of said A2M-2 alleles, wherein a finding that said individual possesses one or more of said A2M-2 alleles indicates that said individual is at risk for developing AD.

2. The method of claim 1, wherein a finding that said individual is homozygous for said A2M-2 allele indicates that said individual is at risk of developing AD.

3. The method of claim 1, wherein a finding that said individual is heterozygous for said A2M-2 allele indicates that said individual is at risk for developing AD.

4. The method of claim 1, wherein said individual has a family member previously diagnosed with AD.

5. The method of claim 1, wherein said genotyping comprises isolating DNA from said individual, amplifying a region of said DNA, wherein said region comprises the site of the pentanucleotide deletion present in the A2M-2 allele, to produce copies of said region, and performing RFLP analysis on said copies.

6. A method used to aid the diagnosis of AD comprising genotyping the A2M locus of an individual suspected to have Alzheimer's disease to determine whether said individual possesses an A2M-2 allele, and drawing a conclusion regarding whether said individual has Alzheimer's disease based on the possession of one or more of said A2M-2 alleles, wherein a finding that said individual possesses one or more of said A2M-2 alleles is an indicator that said individual has AD.

7. The method of claim 6, wherein a finding that said individual is homozygous for said A2M-2 allele is an indicator that said individual has AD.

8. The method of claim 6, wherein a finding that said individual is heterozygous for said A2M-2 allele is an indicator that said individual has AD.

9. The method of claim 6, wherein said individual has a family member previously diagnosed with AD.

10. The method of claim 6, wherein said genotyping comprises isolating DNA from said individual, amplifying a region of said DNA, wherein said region comprises the site of the pentanucleotide deletion present in the A2M-2 allele, to produce copies of said region, and performing RFLP analysis on said copies.

* * * * *

SEQUENCE LISTING

```
<160> NUMBER OF SEQ ID NOS: 4

<210> SEQ ID NO 1
<211> LENGTH: 23
<212> TYPE: DNA
<213> ORGANISM: Homo sapiens

<400> SEQUENCE: 1
ctttccttga tgacccaagc gcc                                            23

<210> SEQ ID NO 2
<211> LENGTH: 22
<212> TYPE: DNA
<213> ORGANISM: Homo sapiens

<400> SEQUENCE: 2
gttgaaaata gtcagcgacc tc                                             22

<210> SEQ ID NO 3
<211> LENGTH: 20
<212> TYPE: DNA
<213> ORGANISM: Homo sapiens

<400> SEQUENCE: 3
atccctgaaa ctgccaccaa                                                20

<210> SEQ ID NO 4
<211> LENGTH: 20
<212> TYPE: DNA
<213> ORGANISM: Homo sapiens

<400> SEQUENCE: 4
gtaactgaaa cctactggaa                                                20
```